US010137305B2

(12) United States Patent
Kane et al.

(10) Patent No.: US 10,137,305 B2
(45) Date of Patent: Nov. 27, 2018

(54) SYSTEMS AND METHODS FOR BEHAVIORALLY RESPONSIVE SIGNAL DETECTION AND THERAPY DELIVERY

(71) Applicant: Cardiac Pacemakers, Inc., St. Paul, MN (US)

(72) Inventors: Michael J. Kane, Roseville, MN (US); William J. Linder, Golden Valley, MN (US); Lance Eric Juffer, Lino Lakes, MN (US); Benjamin J. Haasl, Forest Lake, MN (US); Brian L. Schmidt, White Bear Lake, MN (US); Paul Huelskamp, St. Paul, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 44 days.

(21) Appl. No.: 15/246,172

(22) Filed: Aug. 24, 2016

(65) Prior Publication Data

US 2017/0056664 A1 Mar. 2, 2017

Related U.S. Application Data

(60) Provisional application No. 62/211,359, filed on Aug. 28, 2015.

(51) Int. Cl.
*A61N 1/36* (2006.01)
*A61N 1/365* (2006.01)
(Continued)

(52) U.S. Cl.
CPC ........ *A61N 1/36535* (2013.01); *A61B 5/1116* (2013.01); *A61B 5/1118* (2013.01);
(Continued)

(58) Field of Classification Search
None
See application file for complete search history.

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

AU 2008279789 B2 10/2011
AU 2008329620 B2 5/2014
(Continued)

OTHER PUBLICATIONS

US 8,886,318, 11/2014, Jacobson et al. (withdrawn)
(Continued)

*Primary Examiner* — Ankit D Tejani
(74) *Attorney, Agent, or Firm* — Seager, Tufte & Wickhem LLP

(57) ABSTRACT

Systems, devices, and methods for adjusting functionality of an implantable medical device based on posture are disclosed. In some instances, a method for operating a leadless cardiac pacemaker implanted into a patient, where the patient has two or more predefined behavioral states, may include detecting a change in the behavioral state of the patient, and in response, changing a sampling rate of a sensor signal generated by a sensor of the leadless cardiac pacemaker. In some embodiments, the method may further include using the sampled sensor signal to determine an updated pacing rate of the leadless cardiac pacemaker and providing pacing to the patient at the updated pacing rate.

20 Claims, 10 Drawing Sheets

100
114'
114'
102
120
Communication Module
104
Pulse Generator Module
114
Electrical Sensing Module
106
116
Mechanical Sensing Module
Processing Module
Energy Storage Module
114
108
110
112
114'
114'

(51) Int. Cl.
*A61N 1/375* (2006.01)
*A61N 1/372* (2006.01)
*A61N 1/378* (2006.01)
*A61B 5/11* (2006.01)

(52) U.S. Cl.
CPC ....... *A61N 1/3655* (2013.01); *A61N 1/36521* (2013.01); *A61N 1/36542* (2013.01); *A61N 1/378* (2013.01); *A61N 1/3756* (2013.01); *A61N 1/37247* (2013.01); *A61B 2560/0209* (2013.01)

(56) References Cited

U.S. PATENT DOCUMENTS 4,142,530 A 3/1979 Wittkampf
4,151,513 A 4/1979 Menken et al.
4,157,720 A 6/1979 Greatbatch
RE30,366 E 8/1980 Rasor et al.
4,243,045 A 1/1981 Maas
4,250,884 A 2/1981 Hartlaub et al.
4,256,115 A 3/1981 Bilitch
4,263,919 A 4/1981 Levin
4,310,000 A 1/1982 Lindemans
4,312,354 A 1/1982 Walters
4,323,081 A 4/1982 Wiebusch
4,357,946 A 11/1982 Dutcher et al.
4,365,639 A 12/1982 Goldreyer
4,440,173 A 4/1984 Hudziak et al.
4,476,868 A 10/1984 Thompson
4,522,208 A 6/1985 Buffet
4,537,200 A 8/1985 Widrow
4,556,063 A 12/1985 Thompson et al.
4,562,841 A 1/1986 Brockway et al.
4,593,702 A 6/1986 Kepski et al.
4,593,955 A 6/1986 Leiber
4,630,611 A 12/1986 King
4,635,639 A 1/1987 Hakala et al.
4,674,508 A 6/1987 DeCote
4,712,554 A 12/1987 Garson
4,729,376 A 3/1988 DeCote
4,754,753 A 7/1988 King
4,759,366 A 7/1988 Callaghan
4,776,338 A 10/1988 Lekholm et al.
4,787,389 A 11/1988 Tarjan
4,793,353 A 12/1988 Borkan
4,819,662 A 4/1989 Heil et al.
4,858,610 A 8/1989 Callaghan et al.
4,886,064 A 12/1989 Strandberg
4,887,609 A 12/1989 Cole, Jr.
4,928,688 A 5/1990 Mower
4,967,746 A 11/1990 Vandegriff
4,987,897 A 1/1991 Funke
4,989,602 A 2/1991 Sholder et al.
5,012,806 A 5/1991 De Bellis
5,036,849 A 8/1991 Hauck et al.
5,040,534 A 8/1991 Mann et al.
5,058,581 A 10/1991 Silvian
5,078,134 A 1/1992 Heilman et al.
5,109,845 A 5/1992 Yuuchi et al.
5,113,859 A 5/1992 Funke
5,113,869 A 5/1992 Nappholz et al.
5,117,824 A 6/1992 Keimel et al.
5,127,401 A 7/1992 Grevious et al.
5,133,353 A 7/1992 Hauser
5,144,950 A 9/1992 Stoop et al.
5,170,784 A 12/1992 Ramon et al.
5,179,945 A 1/1993 Van Hofwegen et al.
5,193,539 A 3/1993 Schulman et al.
5,193,540 A 3/1993 Schulman et al.
5,241,961 A 9/1993 Henry
5,243,977 A 9/1993 Trabucco et al.
5,259,387 A 11/1993 dePinto
5,269,326 A 12/1993 Verrier
5,284,136 A 2/1994 Hauck et al.
5,300,107 A 4/1994 Stokes et al.
5,301,677 A 4/1994 Hsung
5,305,760 A 4/1994 McKown et al.
5,312,439 A 5/1994 Loeb
5,313,953 A 5/1994 Yomtov et al.
5,314,459 A 5/1994 Swanson et al.
5,318,597 A 6/1994 Hauck et al.
5,324,316 A 6/1994 Schulman et al.
5,331,966 A 7/1994 Bennett et al.
5,334,222 A 8/1994 Salo et al.
5,342,408 A 8/1994 Decoriolis et al.
5,370,667 A 12/1994 Alt
5,372,606 A 12/1994 Lang et al.
5,376,106 A 12/1994 Stahmann et al.
5,383,915 A 1/1995 Adams
5,388,578 A 2/1995 Yomtov et al.
5,404,877 A 4/1995 Nolan et al.
5,405,367 A 4/1995 Schulman et al.
5,411,031 A 5/1995 Yomtov
5,411,525 A 5/1995 Swanson et al.
5,411,535 A 5/1995 Fujii et al.
5,456,691 A 10/1995 Snell
5,458,622 A 10/1995 Alt
5,466,246 A 11/1995 Silvian
5,468,254 A 11/1995 Hahn et al.
5,472,453 A 12/1995 Alt
5,522,866 A 6/1996 Fernald
5,540,727 A 7/1996 Tockman et al.
5,545,186 A 8/1996 Olson et al.
5,545,202 A 8/1996 Dahl et al.
5,571,146 A 11/1996 Jones et al.
5,591,214 A 1/1997 Lu
5,620,466 A 4/1997 Haefner et al.
5,634,938 A 6/1997 Swanson et al.
5,649,968 A 7/1997 Alt et al.
5,662,688 A 9/1997 Haefner et al.
5,674,259 A 10/1997 Gray
5,683,426 A 11/1997 Greenhut et al.
5,683,432 A 11/1997 Goedeke et al.
5,706,823 A 1/1998 Wodlinger
5,709,215 A 1/1998 Perttu et al.
5,720,770 A 2/1998 Nappholz et al.
5,728,154 A 3/1998 Crossett et al.
5,741,314 A 4/1998 Daly et al.
5,741,315 A 4/1998 Lee et al.
5,752,976 A 5/1998 Duffin et al.
5,752,977 A 5/1998 Grevious et al.
5,755,736 A 5/1998 Gillberg et al.
5,759,199 A 6/1998 Snell et al.
5,774,501 A 6/1998 Halpern et al.
5,792,195 A 8/1998 Carlson et al.
5,792,202 A 8/1998 Rueter
5,792,203 A 8/1998 Schroeppel
5,792,205 A 8/1998 Alt et al.
5,792,208 A 8/1998 Gray
5,814,089 A 9/1998 Stokes et al.
5,827,216 A 10/1998 Igo et al.
5,836,985 A 11/1998 Goyal et al.
5,836,987 A 11/1998 Baumann et al.
5,842,977 A 12/1998 Lesho et al.
5,855,593 A 1/1999 Olson et al.
5,873,894 A 2/1999 Vandegriff et al.
5,891,184 A 4/1999 Lee et al.
5,897,586 A 4/1999 Molina
5,899,876 A 5/1999 Flower
5,899,928 A 5/1999 Sholder et al.
5,919,214 A 7/1999 Ciciarelli et al.
5,935,078 A 8/1999 Feierbach
5,941,906 A 8/1999 Barreras et al.
5,944,744 A 8/1999 Paul et al.
5,954,757 A 9/1999 Gray
5,978,713 A 11/1999 Prutchi et al.
5,991,660 A 11/1999 Goyal
5,991,661 A 11/1999 Park et al.
5,999,848 A 12/1999 Gord et al.
5,999,857 A 12/1999 Weijand et al.
6,002,963 A 12/1999 Mouchawar et al.
6,016,445 A 1/2000 Baura
6,026,320 A 2/2000 Carlson et al.
6,029,085 A 2/2000 Olson et al.

(56) References Cited

U.S. PATENT DOCUMENTS 6,041,250 A 3/2000 dePinto
6,044,297 A 3/2000 Sheldon et al.
6,044,298 A 3/2000 Salo et al.
6,044,300 A 3/2000 Gray
6,055,454 A 4/2000 Heemels
6,073,050 A 6/2000 Griffith
6,076,016 A 6/2000 Feierbach
6,077,236 A 6/2000 Cunningham
6,080,187 A 6/2000 Alt et al.
6,083,248 A 7/2000 Thompson
6,106,551 A 8/2000 Crossett et al.
6,115,636 A 9/2000 Ryan
6,128,526 A 10/2000 Stadler et al.
6,141,581 A 10/2000 Olson et al.
6,141,588 A 10/2000 Cox et al.
6,141,592 A 10/2000 Pauly
6,144,879 A 11/2000 Gray
6,162,195 A 12/2000 Igo et al.
6,164,284 A 12/2000 Schulman et al.
6,167,310 A 12/2000 Grevious
6,201,993 B1 3/2001 Kruse et al.
6,208,894 B1 3/2001 Schulman et al.
6,211,799 B1 4/2001 Post et al.
6,221,011 B1 4/2001 Bardy
6,240,316 B1 5/2001 Richmond et al.
6,240,317 B1 5/2001 Villaseca et al.
6,256,534 B1 7/2001 Dahl
6,259,947 B1 7/2001 Olson et al.
6,266,558 B1 7/2001 Gozani et al.
6,266,567 B1 7/2001 Ishikawa et al.
6,270,457 B1 8/2001 Bardy
6,272,377 B1 8/2001 Sweeney et al.
6,273,856 B1 8/2001 Sun et al.
6,277,072 B1 8/2001 Bardy
6,280,380 B1 8/2001 Bardy
6,285,907 B1 9/2001 Kramer et al.
6,292,698 B1 9/2001 Duffin et al.
6,295,473 B1 9/2001 Rosar
6,297,943 B1 10/2001 Carson
6,298,271 B1 10/2001 Weijand
6,307,751 B1 10/2001 Bodony et al.
6,312,378 B1 11/2001 Bardy
6,315,721 B2 11/2001 Schulman et al.
6,336,903 B1 1/2002 Bardy
6,345,202 B2 2/2002 Richmond et al.
6,351,667 B1 2/2002 Godie
6,351,669 B1 2/2002 Hartley et al.
6,353,759 B1 3/2002 Hartley et al.
6,358,203 B2 3/2002 Bardy
6,361,780 B1 3/2002 Ley et al.
6,368,284 B1 4/2002 Bardy
6,371,922 B1 4/2002 Baumann et al.
6,398,728 B1 6/2002 Bardy
6,400,982 B2 6/2002 Sweeney et al.
6,400,990 B1 6/2002 Silvian
6,408,208 B1 6/2002 Sun
6,409,674 B1 6/2002 Brockway et al.
6,411,848 B2 6/2002 Kramer et al.
6,424,865 B1 7/2002 Ding
6,434,429 B1 8/2002 Kraus et al.
6,438,410 B2 8/2002 Hsu et al.
6,438,417 B1 8/2002 Rockwell et al.
6,438,421 B1 8/2002 Stahmann et al.
6,440,066 B1 8/2002 Bardy
6,441,747 B1 8/2002 Khair et al.
6,442,426 B1 8/2002 Kroll
6,442,432 B2 8/2002 Lee
6,443,891 B1 9/2002 Grevious
6,445,953 B1 9/2002 Bulkes et al.
6,453,200 B1 9/2002 Koslar
6,459,929 B1 10/2002 Hopper et al.
6,466,821 B1 10/2002 Pianca et al.
6,470,215 B1 10/2002 Kraus et al.
6,471,645 B1 10/2002 Warkentin et al.
6,480,745 B2 11/2002 Nelson et al.
6,487,443 B2 11/2002 Olson et al.
6,490,487 B1 12/2002 Kraus et al.
6,498,951 B1 12/2002 Larson et al.
6,507,755 B1 1/2003 Gozani et al.
6,507,759 B1 1/2003 Prutchi et al.
6,512,940 B1 1/2003 Brabec et al.
6,522,915 B1 2/2003 Ceballos et al.
6,526,311 B2 2/2003 Begemann
6,539,253 B2 3/2003 Thompson et al.
6,542,775 B2 4/2003 Ding et al.
6,553,258 B2 4/2003 Stahmann et al.
6,561,975 B1 5/2003 Pool et al.
6,564,807 B1 5/2003 Schulman et al.
6,574,506 B2 6/2003 Kramer et al.
6,584,351 B1 6/2003 Ekwall
6,584,352 B2 6/2003 Combs et al.
6,597,948 B1 7/2003 Rockwell et al.
6,597,951 B2 7/2003 Kramer et al.
6,622,046 B2 9/2003 Fraley et al.
6,628,985 B2 9/2003 Sweeney et al.
6,647,292 B1 11/2003 Bardy et al.
6,658,292 B2 12/2003 Kroll et al.
6,666,844 B1 12/2003 Igo et al.
6,689,117 B2 2/2004 Sweeney et al.
6,690,959 B2 2/2004 Thompson
6,694,189 B2 2/2004 Begemann
6,704,602 B2 3/2004 Berg et al.
6,718,212 B2 4/2004 Parry et al.
6,721,597 B1 4/2004 Bardy et al.
6,738,670 B1 5/2004 Almendinger et al.
6,746,797 B2 6/2004 Benson et al.
6,749,566 B2 6/2004 Russ
6,758,810 B2 7/2004 Lebel et al.
6,763,269 B2 7/2004 Cox
6,778,860 B2 8/2004 Ostroff et al.
6,788,971 B1 9/2004 Sloman et al.
6,788,974 B2 9/2004 Bardy et al.
6,804,558 B2 10/2004 Haller et al.
6,807,442 B1 10/2004 Myklebust et al.
6,847,844 B2 1/2005 Sun et al.
6,871,095 B2 3/2005 Stahmann et al.
6,878,112 B2 4/2005 Linberg et al.
6,885,889 B2 4/2005 Chinchoy
6,892,094 B2 5/2005 Ousdigian et al.
6,897,788 B2 5/2005 Khair et al.
6,904,315 B2 6/2005 Panken et al.
6,907,288 B2 6/2005 Daum
6,922,592 B2 7/2005 Thompson et al.
6,931,282 B2 8/2005 Esler
6,934,585 B1 8/2005 Schloss et al.
6,957,107 B2 10/2005 Rogers et al.
6,978,176 B2 12/2005 Lattouf
6,985,773 B2 1/2006 Von Arx et al.
6,990,375 B2 1/2006 Kloss et al.
7,001,366 B2 2/2006 Ballard
7,003,350 B2 2/2006 Denker et al.
7,006,864 B2 2/2006 Echt et al.
7,013,178 B2 3/2006 Reinke et al.
7,027,871 B2 4/2006 Burnes et al.
7,050,849 B2 5/2006 Echt et al.
7,060,031 B2 6/2006 Webb et al.
7,063,693 B2 6/2006 Guenst
7,082,336 B2 7/2006 Ransbury et al.
7,085,606 B2 8/2006 Flach et al.
7,092,758 B2 8/2006 Sun et al.
7,110,824 B2 9/2006 Amundson et al.
7,120,504 B2 10/2006 Osypka
7,130,681 B2 10/2006 Gebhardt et al.
7,139,613 B2 11/2006 Reinke et al.
7,142,912 B2 11/2006 Wagner et al.
7,146,225 B2 12/2006 Guenst et al.
7,146,226 B2 12/2006 Lau et al.
7,149,581 B2 12/2006 Goedeke
7,149,588 B2 12/2006 Lau et al.
7,158,839 B2 1/2007 Lau
7,162,307 B2 1/2007 Patrias
7,164,952 B2 1/2007 Lau et al.
7,177,700 B1 2/2007 Cox
7,181,505 B2 2/2007 Haller et al.

(56) References Cited

U.S. PATENT DOCUMENTS 7,184,830 B2 2/2007 Echt et al.
7,186,214 B2 3/2007 Ness
7,191,015 B2 3/2007 Lamson et al.
7,200,437 B1 4/2007 Nabutovsky et al.
7,200,439 B2 4/2007 Zdeblick et al.
7,206,423 B1 4/2007 Feng et al.
7,209,785 B2 4/2007 Kim et al.
7,209,790 B2 4/2007 Thompson et al.
7,211,884 B1 5/2007 Davis et al.
7,212,871 B1 5/2007 Morgan
7,225,023 B1 * 5/2007 Park .................. A61N 1/36542 607/19
7,226,440 B2 6/2007 Gelfand et al.
7,228,183 B2 6/2007 Sun et al.
7,236,821 B2 6/2007 Cates et al.
7,236,829 B1 6/2007 Farazi et al.
7,254,448 B2 8/2007 Almendinger et al.
7,260,436 B2 8/2007 Kilgore et al.
7,270,669 B1 9/2007 Sra
7,272,448 B1 9/2007 Morgan et al.
7,277,755 B1 10/2007 Falkenberg et al.
7,280,872 B1 10/2007 Mosesov et al.
7,288,096 B2 10/2007 Chin
7,289,847 B1 10/2007 Gill et al.
7,289,852 B2 10/2007 Helfinstine et al.
7,289,853 B1 10/2007 Campbell et al.
7,289,855 B2 10/2007 Nghiem et al.
7,302,294 B2 11/2007 Kamath et al.
7,305,266 B1 12/2007 Kroll
7,310,556 B2 12/2007 Bulkes
7,319,905 B1 1/2008 Morgan et al.
7,333,853 B2 2/2008 Mazar et al.
7,336,994 B2 2/2008 Hettrick et al.
7,347,819 B2 3/2008 Lebel et al.
7,366,572 B2 4/2008 Heruth et al.
7,373,207 B2 5/2008 Lattouf
7,384,403 B2 6/2008 Sherman
7,386,342 B1 6/2008 Falkenberg et al.
7,389,147 B2 6/2008 Wahlstrand et al.
7,392,090 B2 6/2008 Sweeney et al.
7,406,105 B2 7/2008 DelMain et al.
7,406,349 B2 7/2008 Seeberger et al.
7,410,497 B2 8/2008 Hastings et al.
7,425,200 B2 9/2008 Brockway et al.
7,433,739 B1 10/2008 Salys et al.
7,496,409 B2 2/2009 Greenhut et al.
7,496,410 B2 2/2009 Heil
7,502,652 B2 3/2009 Gaunt et al.
7,512,448 B2 3/2009 Malick et al.
7,515,969 B2 4/2009 Tockman et al.
7,526,342 B2 4/2009 Chin et al.
7,529,589 B2 5/2009 Williams et al.
7,532,933 B2 5/2009 Hastings et al.
7,536,222 B2 5/2009 Bardy et al.
7,536,224 B2 5/2009 Ritscher et al.
7,539,541 B2 5/2009 Quiles et al.
7,544,197 B2 6/2009 Kelsch et al.
7,558,631 B2 7/2009 Cowan et al.
7,565,195 B1 7/2009 Kroll et al.
7,584,002 B2 9/2009 Burnes et al.
7,590,455 B2 9/2009 Heruth et al.
7,606,621 B2 10/2009 Brisken et al.
7,610,088 B2 10/2009 Chinchoy
7,610,092 B2 10/2009 Cowan et al.
7,610,099 B2 10/2009 Almendinger et al.
7,610,104 B2 10/2009 Kaplan et al.
7,616,991 B2 11/2009 Mann et al.
7,617,001 B2 11/2009 Penner et al.
7,617,007 B2 11/2009 Williams et al.
7,630,767 B1 12/2009 Poore et al.
7,634,313 B1 12/2009 Kroll et al.
7,637,867 B2 12/2009 Zdeblick
7,640,060 B2 12/2009 Zdeblick
7,647,109 B2 1/2010 Hastings et al.
7,650,186 B2 1/2010 Hastings et al.
7,657,311 B2 2/2010 Bardy et al.
7,668,596 B2 2/2010 Von Arx et al.
7,682,316 B2 3/2010 Anderson et al.
7,691,047 B2 4/2010 Ferrari
7,702,392 B2 4/2010 Echt et al.
7,713,194 B2 5/2010 Zdeblick
7,713,195 B2 5/2010 Zdeblick
7,729,783 B2 6/2010 Michels et al.
7,734,333 B2 6/2010 Ghanem et al.
7,734,343 B2 6/2010 Ransbury et al.
7,738,958 B2 6/2010 Zdeblick et al.
7,738,964 B2 6/2010 Von Arx et al.
7,742,812 B2 6/2010 Ghanem et al.
7,742,816 B2 6/2010 Masoud et al.
7,742,822 B2 6/2010 Masoud et al.
7,743,151 B2 6/2010 Vallapureddy et al.
7,747,335 B2 6/2010 Williams
7,751,881 B2 7/2010 Cowan et al.
7,758,521 B2 7/2010 Morris et al.
7,761,150 B2 7/2010 Ghanem et al.
7,761,164 B2 7/2010 Verhoef et al.
7,765,001 B2 7/2010 Echt et al.
7,769,452 B2 8/2010 Ghanem et al.
7,783,362 B2 8/2010 Whitehurst et al.
7,792,588 B2 9/2010 Harding
7,797,059 B1 9/2010 Bornzin et al.
7,801,596 B2 9/2010 Fischell et al.
7,809,438 B2 10/2010 Echt et al.
7,822,481 B2 10/2010 Gerber et al.
7,840,281 B2 11/2010 Kveen et al.
7,844,331 B2 11/2010 Li et al.
7,844,348 B2 11/2010 Swoyer et al.
7,846,088 B2 12/2010 Ness
7,848,815 B2 12/2010 Brisken et al.
7,848,823 B2 12/2010 Drasler et al.
7,860,455 B2 12/2010 Fukumoto et al.
7,871,433 B2 1/2011 Lattouf
7,877,136 B1 1/2011 Moffitt et al.
7,877,142 B2 1/2011 Moaddeb et al.
7,881,786 B2 2/2011 Jackson
7,881,798 B2 2/2011 Miesel et al.
7,881,810 B1 2/2011 Chitre et al.
7,890,173 B2 2/2011 Brisken et al.
7,890,181 B2 2/2011 Denzene et al.
7,890,192 B1 2/2011 Kelsch et al.
7,894,885 B2 2/2011 Bartal et al.
7,894,894 B2 2/2011 Stadler et al.
7,894,907 B2 2/2011 Cowan et al.
7,894,910 B2 2/2011 Cowan et al.
7,894,915 B1 2/2011 Chitre et al.
7,899,537 B1 3/2011 Kroll et al.
7,899,541 B2 3/2011 Cowan et al.
7,899,542 B2 3/2011 Cowan et al.
7,899,554 B2 3/2011 Williams et al.
7,901,360 B1 3/2011 Yang et al.
7,904,170 B2 3/2011 Harding
7,907,993 B2 3/2011 Ghanem et al.
7,920,928 B1 4/2011 Yang et al.
7,925,343 B1 4/2011 Min et al.
7,930,022 B2 4/2011 Zhang et al.
7,930,040 B1 4/2011 Kelsch et al.
7,937,135 B2 5/2011 Ghanem et al.
7,937,148 B2 5/2011 Jacobson
7,937,161 B2 5/2011 Hastings et al.
7,941,214 B2 5/2011 Kleckner et al.
7,945,333 B2 5/2011 Jacobson
7,946,997 B2 5/2011 Hübinette
7,949,404 B2 5/2011 Hill
7,949,405 B2 5/2011 Feher
7,953,486 B2 5/2011 Daum et al.
7,953,493 B2 5/2011 Fowler et al.
7,962,202 B2 6/2011 Bhunia
7,974,702 B1 7/2011 Fain et al.
7,979,136 B2 7/2011 Young et al.
7,983,753 B2 7/2011 Severin
3,010,209 A1 8/2011 Jacobson
7,991,467 B2 8/2011 Markowitz et al.
7,991,471 B2 8/2011 Ghanem et al.
7,996,087 B2 8/2011 Cowan et al.

(56) References Cited

U.S. PATENT DOCUMENTS 8,000,791 B2 8/2011 Sunagawa et al.
8,000,807 B2 8/2011 Morris et al.
8,001,975 B2 8/2011 DiSilvestro et al.
8,002,700 B2 8/2011 Ferek-Petric et al.
8,012,098 B2 9/2011 Maile et al.
8,019,419 B1 9/2011 Panescu et al.
8,019,434 B2 9/2011 Quiles et al.
8,027,727 B2 9/2011 Freeberg
8,027,729 B2 9/2011 Sunagawa et al.
8,032,219 B2 10/2011 Neumann et al.
8,036,743 B2 10/2011 Savage et al.
8,046,079 B2 10/2011 Bange et al.
8,046,080 B2 10/2011 Von Arx et al.
8,050,297 B2 11/2011 Delmain et al.
8,050,759 B2 11/2011 Stegemann et al.
8,050,774 B2 11/2011 Kveen et al.
8,055,345 B2 11/2011 Li et al.
8,055,350 B2 11/2011 Roberts
8,060,212 B1 11/2011 Rios et al.
8,065,018 B2 11/2011 Haubrich et al.
8,073,542 B2 12/2011 Doerr
8,078,278 B2 12/2011 Penner
8,078,283 B2 12/2011 Cowan et al.
8,095,123 B2 1/2012 Gray
8,102,789 B2 1/2012 Rosar et al.
8,103,359 B2 1/2012 Reddy
8,103,361 B2 1/2012 Moser
8,112,148 B2 2/2012 Giftakis et al.
8,114,021 B2 2/2012 Robertson et al.
8,121,680 B2 2/2012 Falkenberg et al.
8,123,684 B2 2/2012 Zdeblick
8,126,545 B2 2/2012 Flach et al.
8,131,334 B2 3/2012 Lu et al.
8,140,161 B2 3/2012 Willerton et al.
8,150,521 B2 4/2012 Crowley et al.
8,160,672 B2 4/2012 Kim et al.
8,160,702 B2 4/2012 Mann et al.
8,160,704 B2 4/2012 Freeberg
8,165,694 B2 4/2012 Carbanaru et al.
8,175,715 B1 5/2012 Cox
8,180,451 B2 5/2012 Hickman et al.
8,185,213 B2 5/2012 Kveen et al.
8,187,161 B2 5/2012 Li et al.
8,195,293 B2 6/2012 Limousin et al.
8,204,595 B2 6/2012 Pianca et al.
8,204,605 B2 6/2012 Hastings et al.
8,209,014 B2 6/2012 Doerr
8,214,043 B2 7/2012 Matos
8,224,244 B2 7/2012 Kim et al.
8,229,556 B2 7/2012 Li
8,233,985 B2 7/2012 Bulkes et al.
8,265,748 B2 9/2012 Liu et al.
8,265,757 B2 9/2012 Mass et al.
8,262,578 B1 10/2012 Bharmi et al.
8,280,521 B2 10/2012 Haubrich et al.
8,285,387 B2 10/2012 Utsi et al.
8,290,598 B2 10/2012 Boon et al.
8,290,600 B2 10/2012 Hastings et al.
8,295,939 B2 10/2012 Jacobson
8,301,254 B2 10/2012 Mosesov et al.
8,315,701 B2 11/2012 Cowan et al.
8,315,708 B2 11/2012 Berthelsdorf et al.
8,321,021 B2 11/2012 Kisker et al.
8,321,036 B2 11/2012 Brockway et al.
8,332,036 B2 12/2012 Hastings et al.
8,335,563 B2 12/2012 Stessman
8,335,568 B2 12/2012 Heruth et al.
8,340,750 B2 12/2012 Prakash et al.
8,340,780 B2 12/2012 Hastings et al.
8,352,025 B2 1/2013 Jacobson
8,352,028 B2 1/2013 Wenger
8,352,038 B2 1/2013 Mao et al.
8,359,098 B2 1/2013 Lund et al.
8,364,261 B2 1/2013 Stubbs et al.
8,364,276 B2 1/2013 Willis
8,369,959 B2 2/2013 Meskens
8,369,962 B2 2/2013 Abrahamson
8,380,320 B2 2/2013 Spital
8,386,051 B2 2/2013 Rys
8,391,981 B2 3/2013 Mosesov
8,391,990 B2 3/2013 Smith et al.
8,406,874 B2 3/2013 Liu et al.
8,406,879 B2 3/2013 Shuros et al.
8,406,886 B2 3/2013 Gaunt et al.
8,412,352 B2 4/2013 Griswold et al.
8,417,340 B2 4/2013 Goossen
8,417,341 B2 4/2013 Freeberg
8,423,149 B2 4/2013 Hennig
8,428,722 B2 4/2013 Verhoef et al.
8,433,402 B2 4/2013 Ruben et al.
8,433,409 B2 4/2013 Johnson et al.
8,433,420 B2 4/2013 Bange et al.
8,447,412 B2 5/2013 Dal Molin et al.
8,452,413 B2 5/2013 Young et al.
8,457,740 B2 6/2013 Osche
8,457,742 B2 6/2013 Jacobson
8,457,744 B2 6/2013 Janzig et al.
8,457,761 B2 6/2013 Wariar
8,478,407 B2 7/2013 Demmer et al.
8,478,408 B2 7/2013 Hastings et al.
8,478,431 B2 7/2013 Griswold et al.
8,494,632 B2 7/2013 Sun et al.
8,504,156 B2 8/2013 Bonner et al.
8,509,910 B2 8/2013 Sowder et al.
8,515,559 B2 8/2013 Roberts et al.
8,525,340 B2 9/2013 Eckhardt et al.
8,527,068 B2 9/2013 Ostroff
8,532,790 B2 9/2013 Griswold
8,538,526 B2 9/2013 Stahmann et al.
8,541,131 B2 9/2013 Lund et al.
8,543,205 B2 9/2013 Ostroff
8,547,248 B2 10/2013 Zdeblick et al.
8,548,605 B2 10/2013 Ollivier
8,554,333 B2 10/2013 Wu et al.
8,565,882 B2 10/2013 Matos
8,565,897 B2 10/2013 Regnier et al.
8,571,678 B2 10/2013 Wang
8,577,327 B2 11/2013 Makdissi et al.
8,588,926 B2 11/2013 Moore et al.
8,612,002 B2 12/2013 Faltys et al.
8,615,310 B2 12/2013 Khairkhahan et al.
8,626,280 B2 1/2014 Allavatam et al.
8,626,294 B2 1/2014 Sheldon et al.
8,634,908 B2 1/2014 Cowan
8,634,912 B2 1/2014 Bornzin et al.
8,634,919 B1 1/2014 Hou et al.
8,639,335 B2 1/2014 Peichel et al.
8,644,934 B2 2/2014 Hastings et al.
8,649,859 B2 2/2014 Smith et al.
8,670,842 B1 3/2014 Bornzin et al.
8,676,319 B2 3/2014 Knoll
8,676,335 B2 3/2014 Katoozi et al.
8,700,173 B2 4/2014 Edlund
8,700,181 B2 4/2014 Bornzin et al.
8,705,599 B2 4/2014 dal Molin et al.
8,718,766 B2 5/2014 Wahlberg
8,718,773 B2 5/2014 Willis et al.
8,725,260 B2 5/2014 Shuros et al.
8,738,133 B2 5/2014 Shuros et al.
8,738,147 B2 5/2014 Hastings et al.
8,744,555 B2 6/2014 Allavatam et al.
8,744,572 B1 6/2014 Greenhut et al.
8,747,314 B2 6/2014 Stahmann et al.
8,755,884 B2 6/2014 Demmer et al.
8,758,274 B2 6/2014 Sahasrabudhe et al.
8,758,365 B2 6/2014 Bonner et al.
8,768,483 B2 7/2014 Schmitt et al.
8,774,572 B2 7/2014 Hamamoto
8,781,605 B2 7/2014 Bornzin et al.
8,788,035 B2 7/2014 Jacobson
8,788,053 B2 7/2014 Jacobson
8,798,740 B2 8/2014 Samade et al.
8,798,745 B2 8/2014 Jacobson
8,798,762 B2 8/2014 Fain et al.

(56) References Cited

U.S. PATENT DOCUMENTS 8,798,770 B2 8/2014 Reddy
8,805,505 B1 8/2014 Roberts
8,805,528 B2 8/2014 Corndorf
8,812,109 B2 8/2014 Blomqvist et al.
8,818,504 B2 8/2014 Bodner et al.
8,818,748 B2 8/2014 Hatlestad et al.
8,827,913 B2 9/2014 Havel et al.
8,831,747 B1 9/2014 Min et al.
8,855,789 B2 10/2014 Jacobson
8,868,186 B2 10/2014 Kroll
8,886,339 B2 11/2014 Faltys et al.
8,903,473 B2 12/2014 Rogers et al.
8,903,500 B2 12/2014 Smith et al.
8,903,513 B2 12/2014 Ollivier
8,909,336 B2 12/2014 Navarro-Paredes et al.
8,914,131 B2 12/2014 Bornzin et al.
8,923,795 B2 12/2014 Makdissi et al.
8,923,963 B2 12/2014 Bonner et al.
8,938,300 B2 1/2015 Rosero
8,942,806 B2 1/2015 Sheldon et al.
8,958,892 B2 2/2015 Khairkhahan et al.
8,977,358 B2 3/2015 Ewert et al.
8,989,873 B2 3/2015 Locsin
8,996,109 B2 3/2015 Karst et al.
9,002,467 B2 4/2015 Smith et al.
9,008,776 B2 4/2015 Cowan et al.
9,008,777 B2 4/2015 Dianaty et al.
9,014,818 B2 4/2015 Deterre et al.
9,017,341 B2 4/2015 Bornzin et al.
9,020,611 B2 4/2015 Khairkhahan et al.
9,037,262 B2 5/2015 Regnier et al.
9,042,984 B2 5/2015 Demmer et al.
9,072,911 B2 7/2015 Hastings et al.
9,072,913 B2 7/2015 Jacobson
9,155,882 B2 10/2015 Grubac et al.
9,168,372 B2 10/2015 Fain
9,168,380 B1 10/2015 Greenhut et al.
9,168,383 B2 10/2015 Jacobson et al.
9,180,285 B2 11/2015 Moore et al.
9,192,774 B2 11/2015 Jacobson
9,205,225 B2 12/2015 Khairkhahan et al.
9,216,285 B1 12/2015 Boling et al.
9,216,293 B2 12/2015 Berthiaume et al.
9,216,298 B2 12/2015 Jacobson
9,227,077 B2 1/2016 Jacobson
9,238,145 B2 1/2016 Wenzel et al.
9,242,102 B2 1/2016 Khairkhahan et al.
9,242,113 B2 1/2016 Smith et al.
9,248,300 B2 2/2016 Rys et al.
9,265,436 B2 2/2016 Min et al.
9,265,962 B2 2/2016 Dianaty et al.
9,272,155 B2 3/2016 Ostroff
9,278,218 B2 3/2016 Karst et al.
9,278,229 B1 3/2016 Reinke et al.
9,283,381 B2 3/2016 Grubac et al.
9,283,382 B2 3/2016 Berthiaume et al.
9,289,612 B1 3/2016 Sambelashvili et al.
9,302,115 B2 4/2016 Molin et al.
9,333,364 B2 5/2016 Echt et al.
9,358,387 B2 6/2016 Suwito et al.
9,358,400 B2 6/2016 Jacobson
9,364,675 B2 6/2016 Deterre et al.
9,370,663 B2 6/2016 Moulder
9,375,580 B2 6/2016 Bonner et al.
9,375,581 B2 6/2016 Baru et al.
9,381,365 B2 7/2016 Kibler et al.
9,393,424 B2 7/2016 Demmer et al.
9,393,436 B2 7/2016 Doerr
9,399,139 B2 7/2016 Demmer et al.
9,399,140 B2 7/2016 Cho et al.
9,409,033 B2 8/2016 Jacobson
9,427,594 B1 8/2016 Bornzin et al.
9,433,368 B2 9/2016 Stahmann et al.
9,433,780 B2 9/2016 Régnier et al.
9,492,668 B2 11/2016 Sheldon et al.
9,492,669 B2 11/2016 Demmer et al.
9,492,674 B2 11/2016 Schmidt et al.
9,492,677 B2 11/2016 Greenhut et al.
9,511,233 B2 12/2016 Sambelashvili
9,511,236 B2 12/2016 Varady et al.
9,511,237 B2 12/2016 Deterre et al.
9,522,276 B2 12/2016 Shen et al.
9,522,280 B2 12/2016 Fishier et al.
9,526,522 B2 12/2016 Wood et al.
9,526,891 B2 12/2016 Eggen et al.
9,526,909 B2 12/2016 Stahmann et al.
9,561,382 B2 2/2017 Persson et al.
9,566,012 B2 2/2017 Greenhut et al.
2002/0032470 A1 3/2002 Linberg
2002/0035376 A1 3/2002 Bardy et al.
2002/0035377 A1 3/2002 Bardy et al.
2002/0035378 A1 3/2002 Bardy et al.
2002/0035380 A1 3/2002 Rissmann et al.
2002/0035381 A1 3/2002 Bardy et al.
2002/0042629 A1 4/2002 Bardy et al.
2002/0042630 A1 4/2002 Bardy et al.
2002/0042634 A1 4/2002 Bardy et al.
2002/0049475 A1 4/2002 Bardy et al.
2002/0052636 A1 5/2002 Bardy et al.
2002/0068958 A1 6/2002 Bardy et al.
2002/0072773 A1 6/2002 Bardy et al.
2002/0082665 A1 6/2002 Haller et al.
2002/0091414 A1 7/2002 Bardy et al.
2002/0095196 A1 7/2002 Linberg
2002/0099423 A1 7/2002 Berg et al.
2002/0103510 A1 8/2002 Bardy et al.
2002/0107545 A1 8/2002 Rissmann et al.
2002/0107546 A1 8/2002 Ostroff et al.
2002/0107547 A1 8/2002 Erlinger et al.
2002/0107548 A1 8/2002 Bardy et al.
2002/0107549 A1 8/2002 Bardy et al.
2002/0107559 A1 8/2002 Sanders et al.
2002/0120299 A1 8/2002 Ostroff et al.
2002/0173830 A1 11/2002 Starkweather et al.
2002/0193846 A1 12/2002 Pool et al.
2003/0009203 A1 1/2003 Lebel et al.
2003/0028082 A1 2/2003 Thompson
2003/0040779 A1 2/2003 Engmark et al.
2003/0041866 A1 3/2003 Linberg et al.
2003/0045805 A1 3/2003 Sheldon et al.
2003/0074036 A1* 4/2003 Prutchi .............. A61N 1/37252
607/60
2003/0088278 A1 5/2003 Bardy et al.
2003/0097153 A1 5/2003 Bardy et al.
2003/0105497 A1 6/2003 Zhu et al.
2003/0114908 A1 6/2003 Flach
2003/0144701 A1 7/2003 Mehra et al.
2003/0187460 A1 10/2003 Chin et al.
2003/0187461 A1 10/2003 Chin
2003/0204140 A1 10/2003 Ferek-Patric et al.
2004/0024435 A1 2/2004 Leckrone et al.
2004/0068302 A1 4/2004 Rodgers et al.
2004/0087938 A1 5/2004 Leckrone et al.
2004/0088035 A1 5/2004 Guenst et al.
2004/0102830 A1 5/2004 Williams
2004/0127959 A1 7/2004 Amundson et al.
2004/0133242 A1 7/2004 Chapman et al.
2004/0147969 A1 7/2004 Mann et al.
2004/0147973 A1 7/2004 Hauser
2004/0167558 A1 8/2004 Igo et al.
2004/0167587 A1 8/2004 Thompson
2004/0172071 A1 9/2004 Bardy et al.
2004/0172077 A1 9/2004 Chinchoy
2004/0172104 A1 9/2004 Berg et al.
2004/0176817 A1 9/2004 Wahlstrand et al.
2004/0176818 A1 9/2004 Wahlstrand et al.
2004/0176830 A1 9/2004 Fang
2004/0186529 A1 9/2004 Bardy et al.
2004/0204673 A1 10/2004 Flaherty
2004/0210292 A1 10/2004 Bardy et al.
2004/0210293 A1 10/2004 Bardy et al.
2004/0210294 A1 10/2004 Bardy et al.
2004/0215308 A1 10/2004 Bardy et al.
2004/0220624 A1 11/2004 Ritscher et al.

(56) References Cited

U.S. PATENT DOCUMENTS

2004/0220626 A1 11/2004 Wagner
2004/0220639 A1 11/2004 Mulligan et al.
2004/0249431 A1 12/2004 Ransbury et al.
2004/0260348 A1 12/2004 Bakken et al.
2004/0267303 A1 12/2004 Guenst
2005/0061320 A1 3/2005 Lee et al.
2005/0070962 A1 3/2005 Echt et al.
2005/0102003 A1 5/2005 Grabek et al.
2005/0149138 A1 7/2005 Min et al.
2005/0165466 A1 7/2005 Morris et al.
2005/0182465 A1 8/2005 Ness
2005/0203410 A1 9/2005 Jenkins
2005/0209645 A1 9/2005 Heruth et al.
2005/0283208 A1 12/2005 Von Arx et al.
2005/0288743 A1 12/2005 Ahn et al.
2006/0042830 A1 3/2006 Maghribi et al.
2006/0052829 A1 3/2006 Sun et al.
2006/0052830 A1 3/2006 Spinelli et al.
2006/0064135 A1 3/2006 Brockway
2006/0064149 A1 3/2006 Belacazar et al.
2006/0085039 A1 4/2006 Hastings et al.
2006/0085041 A1 4/2006 Hastings et al.
2006/0085042 A1 4/2006 Hastings et al.
2006/0095078 A1 5/2006 Tronnes
2006/0106442 A1 5/2006 Richardson et al.
2006/0116746 A1 6/2006 Chin
2006/0135999 A1 6/2006 Bodner et al.
2006/0136004 A1 6/2006 Cowan et al.
2006/0161061 A1 7/2006 Echt et al.
2006/0200002 A1 9/2006 Guenst
2006/0206151 A1 9/2006 Lu
2006/0212079 A1 9/2006 Routh et al.
2006/0212080 A1 9/2006 Hartley et al.
2006/0241701 A1 10/2006 Markowitz et al.
2006/0241705 A1 10/2006 Neumann et al.
2006/0247672 A1 11/2006 Vidlund et al.
2006/0259088 A1 11/2006 Pastore et al.
2006/0265018 A1 11/2006 Smith et al.
2007/0004979 A1 1/2007 Wojciechowicz et al.
2007/0016098 A1 1/2007 Kim et al.
2007/0027508 A1 2/2007 Cowan
2007/0078490 A1 4/2007 Cowan et al.
2007/0088394 A1 4/2007 Jacobson
2007/0088396 A1 4/2007 Jacobson
2007/0088397 A1 4/2007 Jacobson
2007/0088398 A1 4/2007 Jacobson
2007/0088405 A1 4/2007 Jacobson
2007/0135882 A1 6/2007 Drasler et al.
2007/0135883 A1 6/2007 Drasler et al.
2007/0150037 A1 6/2007 Hastings et al.
2007/0150038 A1 6/2007 Hastings et al.
2007/0156190 A1 7/2007 Cinbis
2007/0219525 A1 9/2007 Gelfand et al.
2007/0219590 A1 9/2007 Hastings et al.
2007/0225545 A1 9/2007 Ferrari
2007/0233206 A1 10/2007 Frikart et al.
2007/0239244 A1 10/2007 Morgan et al.
2007/0255376 A1 11/2007 Michels et al.
2007/0276444 A1 11/2007 Gelbart et al.
2007/0293900 A1 12/2007 Sheldon et al.
2007/0293904 A1 12/2007 Gelbart et al.
2008/0004663 A1 1/2008 Jorgenson
2008/0021505 A1 1/2008 Hastings et al.
2008/0021519 A1 1/2008 De Geest et al.
2008/0021532 A1 1/2008 Kveen et al.
2008/0065183 A1 3/2008 Whitehurst et al.
2008/0065185 A1 3/2008 Worley
2008/0071318 A1 3/2008 Brooke et al.
2008/0109054 A1 5/2008 Hastings et al.
2008/0119911 A1 5/2008 Rosero
2008/0130670 A1 6/2008 Kim et al.
2008/0154139 A1 6/2008 Shuros et al.
2008/0154322 A1 6/2008 Jackson et al.
2008/0228234 A1 9/2008 Stancer
2008/0234771 A1 9/2008 Chinchoy et al.
2008/0243217 A1 10/2008 Wildon
2008/0269814 A1 10/2008 Rosero
2008/0269825 A1 10/2008 Chinchoy et al.
2008/0275518 A1 11/2008 Ghanem et al.
2008/0275519 A1 11/2008 Ghanem et al.
2008/0281381 A1 11/2008 Gerber et al.
2008/0288039 A1 11/2008 Reddy
2008/0294208 A1 11/2008 Willis et al.
2008/0294210 A1 11/2008 Rosero
2008/0306359 A1 12/2008 Zdeblick et al.
2009/0018599 A1 1/2009 Hastings et al.
2009/0024180 A1 1/2009 Kisker et al.
2009/0036941 A1 2/2009 Corbucci
2009/0048646 A1 2/2009 Katoozi et al.
2009/0062895 A1 3/2009 Stahmann et al.
2009/0082827 A1 3/2009 Kveen et al.
2009/0082828 A1 3/2009 Ostroff
2009/0088813 A1 4/2009 Brockway et al.
2009/0131907 A1 5/2009 Chin et al.
2009/0135886 A1 5/2009 Robertson et al.
2009/0143835 A1 6/2009 Pastore et al.
2009/0171408 A1 7/2009 Solem
2009/0171414 A1 7/2009 Kelly et al.
2009/0204163 A1 8/2009 Shuros et al.
2009/0204170 A1 8/2009 Hastings et al.
2009/0210024 A1 8/2009 M.
2009/0216292 A1 8/2009 Pless et al.
2009/0234407 A1 9/2009 Hastings et al.
2009/0234411 A1 9/2009 Sambelashvili et al.
2009/0266573 A1 10/2009 Engmark et al.
2009/0275998 A1 11/2009 Burnes et al.
2009/0275999 A1 11/2009 Burnes et al.
2009/0299447 A1 12/2009 Jensen et al.
2010/0010380 A1 1/2010 Panken et al.
2010/0013668 A1 1/2010 Kantervik
2010/0016911 A1 1/2010 Willis et al.
2010/0023085 A1 1/2010 Wu et al.
2010/0030061 A1 2/2010 Canfield et al.
2010/0030327 A1 2/2010 Chatel
2010/0042108 A1 2/2010 Hibino
2010/0056871 A1 3/2010 Govari et al.
2010/0063375 A1 3/2010 Kassab et al.
2010/0063562 A1 3/2010 Cowan et al.
2010/0094367 A1 4/2010 Sen
2010/0114209 A1 5/2010 Krause et al.
2010/0114214 A1 5/2010 Morelli et al.
2010/0125281 A1 5/2010 Jacobson et al.
2010/0168761 A1 7/2010 Kassab et al.
2010/0168819 A1 7/2010 Freeberg
2010/0198288 A1 8/2010 Ostroff
2010/0198304 A1 8/2010 Wang
2010/0217367 A1 8/2010 Belson
2010/0228308 A1 9/2010 Cowan et al.
2010/0234906 A1 9/2010 Koh
2010/0234924 A1 9/2010 Willis
2010/0241185 A1 9/2010 Mahapatra et al.
2010/0249729 A1 9/2010 Morris et al.
2010/0280500 A1 11/2010 Skelton et al.
2010/0286744 A1 11/2010 Echt et al.
2010/0312309 A1 12/2010 Harding
2011/0022113 A1 1/2011 Zdeblick et al.
2011/0071586 A1 3/2011 Jacobson
2011/0077708 A1 3/2011 Ostroff
2011/0112600 A1 5/2011 Cowan et al.
2011/0118588 A1 5/2011 Komblau et al.
2011/0118810 A1 5/2011 Cowan et al.
2011/0137187 A1 6/2011 Yang et al.
2011/0144720 A1 6/2011 Cowan et al.
2011/0152970 A1 6/2011 Jollota et al.
2011/0160558 A1 6/2011 Rassatt et al.
2011/0160565 A1 6/2011 Stubbs et al.
2011/0160801 A1 6/2011 Markowitz et al.
2011/0160806 A1 6/2011 Lyden et al.
2011/0166620 A1 7/2011 Cowan et al.
2011/0166621 A1 7/2011 Cowan et al.
2011/0184491 A1 7/2011 Kivi
2011/0190835 A1 8/2011 Brockway et al.
2011/0208260 A1 8/2011 Jacobson
2011/0218587 A1 9/2011 Jacobson

(56) References Cited

U.S. PATENT DOCUMENTS

2011/0230734 A1 9/2011 Fain et al.
2011/0237967 A1 9/2011 Moore et al.
2011/0245890 A1 10/2011 Brisben et al.
2011/0251660 A1 10/2011 Griswold
2011/0251662 A1 10/2011 Griswold et al.
2011/0270099 A1 11/2011 Ruben et al.
2011/0270339 A1 11/2011 Murray, III et al.
2011/0270340 A1 11/2011 Pellegrini et al.
2011/0276102 A1 11/2011 Cohen
2011/0282423 A1 11/2011 Jacobson
2012/0004527 A1 1/2012 Thompson et al.
2012/0029323 A1 2/2012 Zhao
2012/0041508 A1 2/2012 Rousso et al.
2012/0059433 A1 3/2012 Cowan et al.
2012/0059436 A1 3/2012 Fontaine et al.
2012/0065500 A1 3/2012 Rogers et al.
2012/0078322 A1 3/2012 Dal Molin et al.
2012/0089198 A1 4/2012 Ostroff
2012/0093245 A1 4/2012 Makdissi et al.
2012/0095521 A1 4/2012 Hintz
2012/0095539 A1 4/2012 Khairkhahan et al.
2012/0101540 A1 4/2012 O'Brien et al.
2012/0101553 A1 4/2012 Reddy
2012/0109148 A1 5/2012 Bonner et al.
2012/0109149 A1 5/2012 Bonner et al.
2012/0109236 A1 5/2012 Jacobson et al.
2012/0109259 A1 5/2012 Bond et al.
2012/0116489 A1 5/2012 Khairkhahan et al.
2012/0150251 A1 6/2012 Giftakis et al.
2012/0158111 A1 6/2012 Khairkhahan et al.
2012/0165827 A1 6/2012 Khairkhahan et al.
2012/0172690 A1 7/2012 Anderson et al.
2012/0172891 A1 7/2012 Lee
2012/0172892 A1 7/2012 Grubac et al.
2012/0172942 A1 7/2012 Berg
2012/0197350 A1 8/2012 Roberts et al.
2012/0197373 A1 8/2012 Khairkhahan et al.
2012/0215285 A1 8/2012 Tahmasian et al.
2012/0232565 A1 9/2012 Kveen et al.
2012/0277600 A1 11/2012 Greenhut
2012/0277606 A1 11/2012 Ellingson et al.
2012/0283795 A1 11/2012 Stancer et al.
2012/0283807 A1 11/2012 Deterre et al.
2012/0290025 A1 11/2012 Keimel
2012/0296381 A1 11/2012 Matos
2012/0303082 A1 11/2012 Dong et al.
2012/0316613 A1 12/2012 Keefe et al.
2013/0012151 A1 1/2013 Hankins
2013/0023975 A1 1/2013 Locsin
2013/0035748 A1 2/2013 Bonner et al.
2013/0041422 A1 2/2013 Jacobson
2013/0053908 A1 2/2013 Smith et al.
2013/0053915 A1 2/2013 Holmstrom et al.
2013/0053921 A1 2/2013 Bonner et al.
2013/0060298 A1 3/2013 Splett et al.
2013/0066169 A1 3/2013 Rys et al.
2013/0072770 A1 3/2013 Rao et al.
2013/0079798 A1 3/2013 Tran et al.
2013/0079861 A1 3/2013 Reinert et al.
2013/0085350 A1 4/2013 Schugt et al.
2013/0085403 A1 4/2013 Gunderson et al.
2013/0085550 A1 4/2013 Polefko et al.
2013/0096649 A1 4/2013 Martin et al.
2013/0103047 A1 4/2013 Steingisser et al.
2013/0103109 A1 4/2013 Jacobson
2013/0110008 A1 5/2013 Bourget et al.
2013/0110127 A1 5/2013 Bornzin et al.
2013/0110192 A1 5/2013 Tran et al.
2013/0110219 A1 5/2013 Bornzin et al.
2013/0116529 A1 5/2013 Min et al.
2013/0116738 A1 5/2013 Samade et al.
2013/0116740 A1 5/2013 Bornzin et al.
2013/0116741 A1 5/2013 Bornzin et al.
2013/0123872 A1 5/2013 Bornzin et al.
2013/0123875 A1 5/2013 Varady et al.
2013/0131591 A1 5/2013 Berthiaume et al.
2013/0131693 A1 5/2013 Berthiaume et al.
2013/0138006 A1 5/2013 Bornzin et al.
2013/0150695 A1 6/2013 Biela et al.
2013/0150911 A1 6/2013 Perschbacher et al.
2013/0150912 A1 6/2013 Perschbacher et al.
2013/0184776 A1 7/2013 Shuros et al.
2013/0196703 A1 8/2013 Masoud et al.
2013/0197609 A1 8/2013 Moore et al.
2013/0231710 A1 9/2013 Jacobson
2013/0238072 A1 9/2013 Deterre et al.
2013/0238073 A1 9/2013 Makdissi et al.
2013/0253342 A1 9/2013 Griswold et al.
2013/0253343 A1 9/2013 Waldhauser et al.
2013/0253344 A1 9/2013 Griswold et al.
2013/0253345 A1 9/2013 Griswold et al.
2013/0253346 A1 9/2013 Griswold et al.
2013/0253347 A1 9/2013 Griswold et al.
2013/0261497 A1 10/2013 Pertijs et al.
2013/0265144 A1 10/2013 Banna et al.
2013/0268042 A1 10/2013 Hastings et al.
2013/0274828 A1 10/2013 Willis
2013/0274847 A1 10/2013 Ostroff
2013/0282070 A1 10/2013 Cowan et al.
2013/0282073 A1 10/2013 Cowan et al.
2013/0289667 A1 10/2013 Wacnik et al.
2013/0296727 A1 11/2013 Sullivan et al.
2013/0303872 A1 11/2013 Taff et al.
2013/0324825 A1 12/2013 Ostroff et al.
2013/0325081 A1 12/2013 Karst et al.
2013/0345770 A1 12/2013 Dianaty et al.
2014/0012344 A1 1/2014 Hastings et al.
2014/0018876 A1 1/2014 Ostroff
2014/0018877 A1 1/2014 Demmer et al.
2014/0031836 A1 1/2014 Ollivier
2014/0039570 A1 2/2014 Carroll et al.
2014/0039591 A1 2/2014 Drasler et al.
2014/0043146 A1 2/2014 Makdissi et al.
2014/0046395 A1 2/2014 Regnier et al.
2014/0046420 A1 2/2014 Moore et al.
2014/0058240 A1 2/2014 Mothilal et al.
2014/0058494 A1 2/2014 Ostroff et al.
2014/0074114 A1 3/2014 Khairkhahan et al.
2014/0074186 A1 3/2014 Faltys et al.
2014/0094891 A1 4/2014 Pare et al.
2014/0100627 A1 4/2014 Min
2014/0107723 A1 4/2014 Hou et al.
2014/0121719 A1 5/2014 Bonner et al.
2014/0121720 A1 5/2014 Bonner et al.
2014/0121722 A1 5/2014 Sheldon et al.
2014/0128935 A1 5/2014 Kumar et al.
2014/0135865 A1 5/2014 Hastings et al.
2014/0142648 A1 5/2014 Smith et al.
2014/0148675 A1 5/2014 Nordstrom et al.
2014/0148815 A1 5/2014 Wenzel et al.
2014/0155950 A1 6/2014 Hastings et al.
2014/0169162 A1 6/2014 Romano et al.
2014/0172060 A1 6/2014 Bornzin et al.
2014/0180306 A1 6/2014 Grubac et al.
2014/0180366 A1 6/2014 Edlund
2014/0207149 A1 7/2014 Hastings et al.
2014/0207210 A1 7/2014 Willis et al.
2014/0214104 A1 7/2014 Greenhut et al.
2014/0222098 A1 8/2014 Baru et al.
2014/0222109 A1 8/2014 Moulder
2014/0228913 A1 8/2014 Molin et al.
2014/0236172 A1 8/2014 Hastings et al.
2014/0243848 A1 8/2014 Auricchio et al.
2014/0255298 A1 9/2014 Cole et al.
2014/0257324 A1 9/2014 Fain
2014/0257422 A1 9/2014 Herken
2014/0257444 A1 9/2014 Cole et al.
2014/0276929 A1 9/2014 Foster et al.
2014/0303704 A1 10/2014 Suwito et al.
2014/0309706 A1 10/2014 Jacobson
2014/0379041 A1 12/2014 Foster
2015/0025612 A1 1/2015 Haasl et al.
2015/0039041 A1 2/2015 Smith et al.
2015/0051609 A1 2/2015 Schmidt et al.

(56) References Cited

U.S. PATENT DOCUMENTS

2015/0051610 A1 2/2015 Schmidt et al.
2015/0051611 A1 2/2015 Schmidt et al.
2015/0051612 A1 2/2015 Schmidt et al.
2015/0051613 A1 2/2015 Schmidt et al.
2015/0051614 A1 2/2015 Schmidt et al.
2015/0051615 A1 2/2015 Schmidt et al.
2015/0051616 A1 2/2015 Haasl et al.
2015/0051682 A1 2/2015 Schmidt et al.
2015/0057520 A1 2/2015 Foster et al.
2015/0057558 A1 2/2015 Stahmann et al.
2015/0057721 A1 2/2015 Stahmann et al.
2015/0088155 A1 3/2015 Stahmann et al.
2015/0105836 A1 4/2015 Bonner et al.
2015/0157861 A1 6/2015 Aghassian
2015/0173655 A1 6/2015 Demmer et al.
2015/0190638 A1 7/2015 Smith et al.
2015/0196756 A1 7/2015 Stahmann et al.
2015/0196757 A1 7/2015 Stahmann et al.
2015/0196758 A1 7/2015 Stahmann et al.
2015/0196769 A1 7/2015 Stahmann et al.
2015/0217119 A1 8/2015 Nikolski et al.
2015/0221898 A1 8/2015 Chi et al.
2015/0224315 A1 8/2015 Stahmann
2015/0224320 A1 8/2015 Stahmann
2015/0258345 A1 9/2015 Smith et al.
2015/0290468 A1 10/2015 Zhang
2015/0297905 A1 10/2015 Greenhut et al.
2015/0297907 A1 10/2015 Zhang
2015/0305637 A1 10/2015 Greenhut et al.
2015/0305638 A1 10/2015 Zhang
2015/0305639 A1 10/2015 Greenhut et al.
2015/0305640 A1 10/2015 Reinke et al.
2015/0305641 A1 10/2015 Stadler et al.
2015/0305642 A1 10/2015 Reinke et al.
2015/0306374 A1 10/2015 Seifert et al.
2015/0306375 A1 10/2015 Marshall et al.
2015/0306406 A1 10/2015 Crutchfield et al.
2015/0306407 A1 10/2015 Crutchfield et al.
2015/0306408 A1 10/2015 Greenhut et al.
2015/0321016 A1 11/2015 O'Brien et al.
2015/0328459 A1 11/2015 Chin et al.
2016/0015322 A1 1/2016 Anderson et al.
2016/0023000 A1 1/2016 Cho et al.
2016/0030757 A1 2/2016 Jacobson
2016/0033177 A1 2/2016 Barot et al.
2016/0121127 A1 5/2016 Klimovitch et al.
2016/0121128 A1 5/2016 Fishler et al.
2016/0121129 A1 5/2016 Persson et al.
2016/0175603 A1* 6/2016 Sheldon ............... A61N 1/3962 607/4
2016/0213919 A1 7/2016 Suwito et al.
2016/0213937 A1 7/2016 Reinke et al.
2016/0213939 A1 7/2016 Carney et al.
2016/0228026 A1 8/2016 Jackson
2016/0317825 A1 11/2016 Jacobson
2016/0367823 A1 12/2016 Cowan et al.
2017/0014629 A1 1/2017 Ghosh et al.
2017/0035315 A1 2/2017 Jackson
2017/0043173 A1 2/2017 Sharma et al.
2017/0043174 A1 2/2017 Greenhut et al.

FOREIGN PATENT DOCUMENTS

AU 2014203793 A1 7/2014
CA 1003904 A1 1/1977
CN 202933393 U 5/2013
EP 0362611 A1 4/1990
EP 503823 A2 9/1992
EP 1070516 A2 1/2001
EP 1702648 A2 9/2006
EP 1904166 B1 6/2011
EP 2433675 B1 1/2013
EP 2441491 B1 1/2013
EP 2452721 B1 11/2013
EP 1948296 B1 1/2014
EP 2662113 A3 1/2014
EP 2471452 B1 12/2014
EP 2760541 B1 5/2016
EP 2833966 B1 5/2016
JP 2000051373 A 2/2000
JP 2002502640 A 1/2002
JP 2004512105 A 4/2004
JP 2005508208 A 3/2005
JP 2005245215 A 9/2005
JP 2008540040 A 11/2008
JP 5199867 B2 2/2013
WO 9500202 A1 1/1995
WO 9636134 A1 11/1996
WO 9724981 A2 7/1997
WO 9826840 A1 6/1998
WO 9939767 A1 8/1999
WO 0234330 A2 1/2003
WO 02098282 A2 5/2003
WO 2005000206 A3 4/2005
WO 2005042089 A1 5/2005
WO 2006065394 A1 6/2006
WO 2006086435 A3 8/2006
WO 2006113659 A1 10/2006
WO 2006124833 A2 11/2006
WO 2006124833 A3 5/2007
WO 2007075974 A2 7/2007
WO 2009006531 A1 1/2009
WO 2012054102 A1 4/2012
WO 2013058958 A1 4/2013
WO 2013080038 A2 6/2013
WO 2013086363 A2 6/2013
WO 2013098644 A3 8/2013
WO 2013184787 A1 12/2013
WO 2014120769 A1 8/2014
WO 2014194240 A1 12/2014

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering,vol. 60(8): 2067-2079, 2013.
Wegmüller, "Intra-Body Communication for Biomedical Sensor Networks," Diss. ETH, No. 17323, 1-173, 2007.
Notification of Transmittal of the International Search Report and the Written Opinion of the International Searching Authority, or the Declaration, dated Jan. 29, 2016, 15 pages.
Spickler et al., "Totally Self-Contained Intracardiac Pacemaker," Journal of Electrocardiology, vol. 3(3&4): 324-331, 1970.
"Instructions for Use System 1, Leadless Cardiac Pacemaker (LCP) and Delivery Catheter," Nanostim Leadless Pacemakers, pp. 1-28, 2013.
International Search Report and Written Opinion for Application No. PCT/US2016/048444, 15 pages, dated Nov. 26, 2016.

* cited by examiner

SYSTEMS AND METHODS FOR BEHAVIORALLY RESPONSIVE SIGNAL DETECTION AND THERAPY DELIVERY

CROSS REFERENCE TO RELATED APPLICATION

This application claims the benefit of U.S. Provisional Patent Application Ser. No. 62/211,359 filed on Aug. 28, 2015, the disclosure of which is incorporated herein by reference.

TECHNICAL FIELD

The present disclosure generally relates to systems, devices, and methods for detecting positional and behavioral states of a patient, and more particularly, to systems, devices, and methods for adapting sensing and therapy delivery based on the detected positional and behavioral states of a patient.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, such devices may adjust their operation based on patient related characteristics.

SUMMARY

The present disclosure generally relates to systems, devices, and methods for detecting positional and/or behavioral states of a patient, and more particularly, to systems, devices, and methods for adapting sensing and/or therapy delivery based on the detected positional and/or behavioral states of a patient. In a first illustrative embodiment, a leadless cardiac pacemaker (LCP) may comprise a plurality of electrodes, a sensor, and a controller connected to the plurality of electrodes and the sensor. In some embodiments, the controller may be configured to detect a change in a behavioral state, in response to detecting that change in the behavioral state, change a sampling rate of a sensor signal generated by the sensor, and determine, using the sampled sensor signal, an updated pacing rate. In some instances, the controller may be further configured to deliver pacing pulses to the plurality of electrodes based on the updated pacing rate.

Additionally, or alternatively, in the first illustrative embodiment, the sensor may have a lower power mode and a higher power mode, and the controller may further be configured to use the sensor in the lower power mode to detect the change in the behavioral state and, in response to detecting the change in the behavioral state, switch the sensor to the higher power mode.

Additionally, or alternatively, in any of the above embodiments with respect to the first illustrative embodiment, the lower power mode may be a low power sleep mode, and the higher power mode may be an awake mode.

Additionally, or alternatively, in any of the above embodiments with respect to the first illustrative embodiment, the change in the behavioral state may correspond to a change in a posture.

Additionally, or alternatively, in any of the above embodiments with respect to the first illustrative embodiment, the change in the behavioral state may correspond to a change in an activity level.

Additionally, or alternatively, in any of the above embodiments with respect to the first illustrative embodiment, the sensor may be an accelerometer.

Additionally, or alternatively, in any of the above embodiments with respect to the first illustrative embodiment, the sensor may be one or more of an impedance sensor, a pressure sensor, a flow sensor, a temperature sensor, a gyroscope, an acoustic sensor and a blood oxygenation sensor.

Additionally, or alternatively, in any of the above embodiments with respect to the first illustrative embodiment, in response to detecting the change in the behavioral state of the patient, the controller may be further configured to change a sampling time window for sampling the sensor signal generated by the sensor.

Additionally, or alternatively, in any of the above embodiments with respect to the first illustrative embodiment, upon detecting a change from an inactive behavioral state to an active behavioral state, the leadless cardiac pacemaker may determine an updated pacing rate that is increased to reduce orthostatic tension in the patient.

Additionally, or alternatively, in any of the above embodiments with respect to the first illustrative embodiment, upon detecting a change from the active behavioral state to the inactive behavioral state, the controller is may be further configured to determine an updated pacing rate that is decreased.

Additionally, or alternatively, in any of the above embodiments with respect to the first illustrative embodiment, upon detecting a change from the active behavioral state to the inactive behavioral state, the controller may be further configured to decrease the sampling rate of the sensor signal generated by the sensor.

Additionally, or alternatively, in any of the above embodiments with respect to the first illustrative embodiment, upon detecting a change from the inactive behavioral state to the active behavioral state, the controller may be further configured to increase the sampling rate of the sensor signal generated by the sensor.

Additionally, or alternatively, in any of the above embodiments with respect to the first illustrative embodiment, upon detecting a change from the active behavioral state to the inactive behavioral state, the controller may be further configured to lower the lower-rate-limit (LRL), and upon detecting a change from the inactive behavioral state to the active behavioral state, the controller is further configured to raise the lower-rate-limit (LRL).

In a second illustrative embodiment, a method may comprise sensing, with a leadless cardiac pacemaker, a predetermined physiological parameter using a sensor, the leadless cardiac pacemaker capable of sensing the predetermined physiological parameter in a lower power sensing mode with less resolution and a higher power sensing mode with more resolution and detecting a change, with the leadless cardiac pacemaker, from a first one of the two or more predefined postures to a second one of the two or more predefined postures, and in response, the leadless cardiac pacemaker changing from the lower power sensing mode to the higher power sensing mode. In some further embodiments, the method may further comprise using the sensed physiological parameter, by the leadless cardiac pacemaker, to determine an updated pacing rate of the leadless cardiac pacemaker. In still some further embodiments, the method may comprise the leadless cardiac pacemaker providing pacing to the patient at the updated pacing rate.

Additionally, or alternatively, in any of the above embodiments with respect to the second illustrative embodiment, the method may further comprise detecting, by the leadless cardiac pacemaker, a change from the second one of the two or more predefined postures to the first one of the two or more predefined postures, and in response, changing, by the leadless cardiac pacemaker, from the higher power sensing mode to the lower power sensing mode.

In a third illustrative embodiment, a method for operating a leadless cardiac pacemaker implanted into a patient, the patient having two or more predefined behavioral states, may comprise the leadless cardiac pacemaker may detect a change in the behavioral state of the patient, and in response, the leadless cardiac pacemaker may change a sampling rate of a sensor signal generated by a sensor of the leadless cardiac pacemaker and the leadless cardiac pacemaker may use the sampled sensor signal to determine an updated pacing rate of the leadless cardiac pacemaker. In some further embodiments, the leadless cardiac pacemaker may provide pacing to the patient at the updated pacing rate.

Additionally, or alternatively, in the third illustrative embodiment, the sensor may have a lower power mode and a higher power mode, and wherein the leadless cardiac pacemaker may use the sensor in the lower power mode to detect the change in the behavioral state of the patient, and in response to detecting the change in the behavioral state of the patient, the leadless cardiac pacemaker may switch the sensor to the higher power mode.

Additionally, or alternatively, in any of the above embodiments with respect to the third illustrative embodiment, the lower power mode may be a low power sleep mode, and the higher power mode may be an awake mode.

Additionally, or alternatively, in any of the above embodiments with respect to the third illustrative embodiment, the change in the behavioral state may correspond to a change in a posture of the patient.

Additionally, or alternatively, in any of the above embodiments with respect to the third illustrative embodiment, the change in the behavioral state may correspond to a change in an activity level of the patient.

Additionally, or alternatively, in any of the above embodiments with respect to the third illustrative embodiment, the sensor may be an accelerometer.

Additionally, or alternatively, in any of the above embodiments with respect to the third illustrative embodiment, the sensor may be one or more of an impedance sensor, a pressure sensor, a flow sensor, a temperature sensor, a gyroscope, an acoustic sensor and a blood oxygenation sensor.

Additionally, or alternatively, in any of the above embodiments with respect to the third illustrative embodiment, in response to detecting the change in the behavioral state of the patient, the leadless cardiac pacemaker may further change a sampling time window for sampling the sensor signal generated by the sensor of the leadless cardiac pacemaker.

Additionally, or alternatively, in any of the above embodiments with respect to the third illustrative embodiment, upon detecting a change from an inactive behavioral state to an active behavioral state, the leadless cardiac pacemaker may determine an updated pacing rate that is increased to reduce orthostatic tension in the patient.

Additionally, or alternatively, in any of the above embodiments with respect to the third illustrative embodiment, upon detecting a change from the active behavioral state to the inactive behavioral state, the leadless cardiac pacemaker may determine an updated pacing rate that is decreased.

Additionally, or alternatively, in any of the above embodiments with respect to the third illustrative embodiment, upon detecting a change from the active behavioral state to the inactive behavioral state, the leadless cardiac pacemaker may decrease the sampling rate of the sensor signal generated by the sensor of the leadless cardiac pacemaker.

Additionally, or alternatively, in any of the above embodiments with respect to the third illustrative embodiment, upon detecting a change from the inactive behavioral state to the active behavioral state, the leadless cardiac pacemaker may increase the sampling rate of the sensor signal generated by the sensor of the leadless cardiac pacemaker.

Additionally, or alternatively, in any of the above embodiments with respect to the third illustrative embodiment, upon detecting a change from the active behavioral state to the inactive behavioral state, the leadless cardiac pacemaker may lower the lower-rate-limit (LRL), and upon detecting a change from the inactive behavioral state to the active behavioral state, the leadless cardiac pacemaker may raise the lower-rate-limit (LRL).

Additionally, or alternatively, in any of the above embodiments with respect to the third illustrative embodiment, the method may further comprise receiving input from a user that defines one or more of the behavioral states, wherein the input is received via communication messages from an external programmer.

In a fourth illustrative embodiment, a leadless cardiac pacemaker (LCP) may comprise a plurality of electrodes, an accelerometer, and a controller connected to the plurality of electrodes and the accelerometer. In some embodiments, the controller may be configured to sense an acceleration signal generated by the accelerometer, the controller capable of sensing the acceleration signal in a lower power sensing mode with less resolution and a higher power sensing mode with more resolution and detect a change from a first one of two or more predefined postures via the acceleration signal to a second one of the two or more predefined postures, and in response, change from the lower power sensing mode to the higher power sensing mode. In some further embodiments, the controller may be configured to use the sensed acceleration signal to determine an updated pacing rate. In some still further embodiments, the controller may be configured to provide pacing to the patient at the updated pacing rate.

Additionally, or alternatively, in any of the above embodiments with respect to the fourth illustrative embodiment, in the higher power sensing mode, the acceleration signal may be sampled at a higher sampling rate than in the lower power sensing mode.

Additionally, or alternatively, in any of the above embodiments with respect to the fourth illustrative embodiment, in the higher power sensing mode, the acceleration signal may be sampled in a longer sampling time window than in the lower power sensing mode.

Additionally, or alternatively, in any of the above embodiments with respect to the fourth illustrative embodiment, the pacing may be provided via two or more of the plurality of electrodes.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
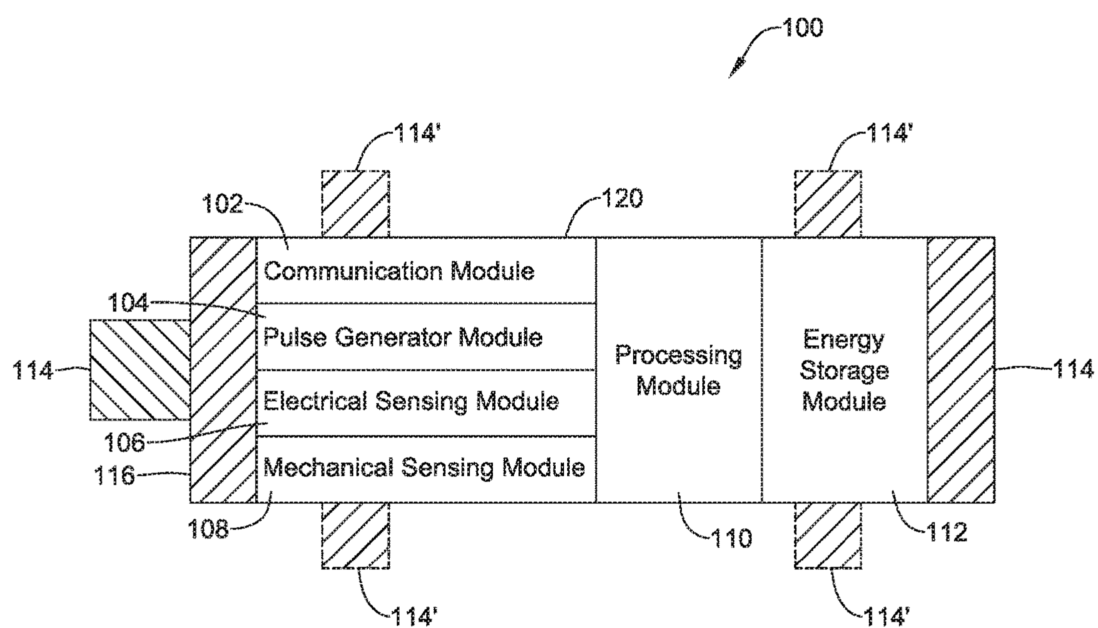
FIG. 1 is a schematic block diagram of an illustrative leadless cardiac pacemaker (LCP) according to one embodiment of the present disclosure.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

FIG. 1 is a conceptual schematic block diagram of an exemplary leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, LCP 100 may vary the rate at which pulse generator module 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neurostimulation therapy or the like. Pulse generator module 104 may include one or more capacitor elements and/or other charge storage devices to aid in generating and delivering appropriate electrical stimulation pulses. In at least some embodiments, pulse generator module 104 may use energy stored in energy storage module 112 to generate the electrical stimulation pulses. In some particular embodiments, pulse generator module 104 may include a switching circuit that is connected to energy storage module 112 and may connect energy storage module 112 to one or more of electrodes 114/114' to generate electrical stimulation pulses.

LCP 100 may further include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, including multi-axis accelerometers such as two- or three-axis accelerometers or other gravitational axis sensors, gyroscopes, including multi-axis gyroscopes such as two- or three-axis gyroscopes, blood pressure sensors, flow sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

Processing module 110 may be configured to direct the operation of LCP 100 and may, in some embodiments, be termed a controller. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias and other determinations such as whether LCP 100 has become dislodged. Processing module 110 may further receive information from communication module 102. In some embodiments, processing module 110 may additionally use such received information to determine occurrences and types of arrhythmias and/or and other determinations such as whether LCP 100 has become dislodged. In still some additional embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining an occurrence of an arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, processing module 110 may monitor one or more physiological parameters of the patient which may indicate a need for an increased heart rate (e.g. due to increased metabolic demand). Processing module 110 may then increase the rate at which pulse generator module 104 generates electrical stimulation pulses. Adjusting the rate of delivery of the electrical stimulation pulses based on the one or more physiological parameters may extend the battery life of LCP 100 by only requiring higher rates of delivery of electrical stimulation pulses when the physiological parameters indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In CRT, processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In further embodiments, processing module 110 may control switching circuitry by which communication module 102 and pulse generator module 104 deliver communication signals and/or electrical stimulation pulses to tissue of the patient. As described above, both communication module 102 and pulse generator module 104 may include circuitry for connecting one or more electrodes 114 and/114' to communication module 102 and/or pulse generator module 104 so those modules may deliver the communication signals and electrical stimulation pulses to tissue of the patient. The specific combination of one or more electrodes by which communication module 102 and/or pulse generator module 104 deliver communication signals and electrical stimulation pulses may influence the reception of communication signals and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip. In still other embodiments, processing module 110 may not be a single component. For example, processing module 110 may include multiple components positioned at disparate locations within LCP 100 in order to perform the various described functions. For example, certain functions may be performed in one component of processing module 110, while other functions are performed in a separate component of processing module 110.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as capacitors or super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy. In embodiments where LCP 100 includes an accelerometer, LCP 100 may additionally be able to sense the motion of the cardiac wall to which LCP 100 is attached.

Figure 2:
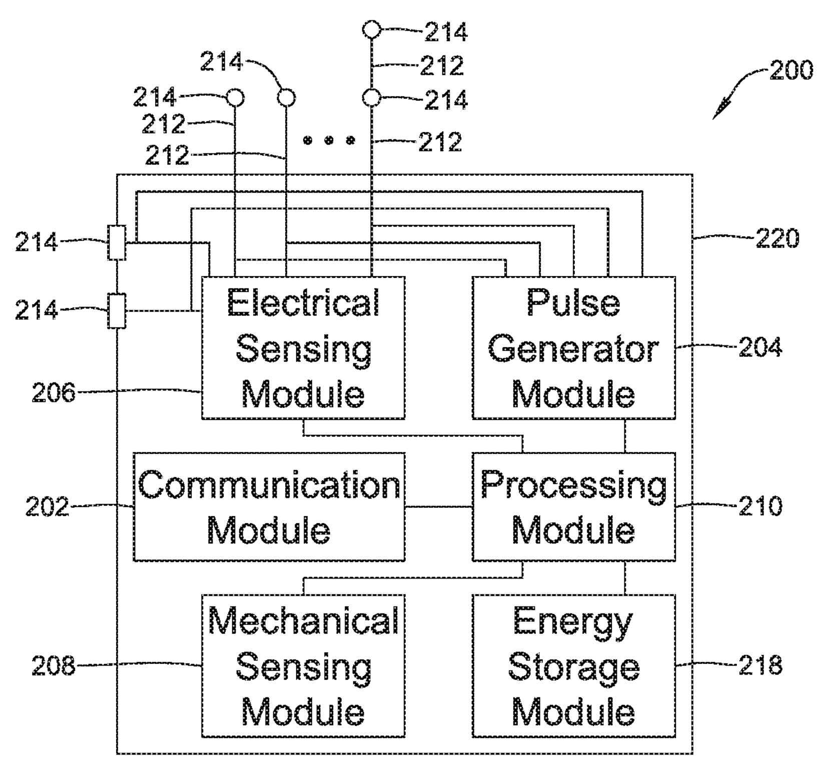
FIG. 2 is a schematic block diagram of another illustrative medical device that may be used in conjunction with the LCP of FIG. 1.

FIG. 2 depicts an embodiment of another device, medical device (MD) 200, which may operate to sense physiological signals and parameters and deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. However, in some embodiments, MD 200 may have a larger volume within housing 220. In such embodiments, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead

212. For example, one or more electrodes 214 may be connected directly to housing 220.

Leads 212, in some embodiments, may additionally contain one or more sensors, such as accelerometers, gyroscopes, blood pressure sensors, flow sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MD 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). MD 200 may further be configured to deliver various types of electrical stimulation therapy, including, for example, defibrillation therapy via skin-electrodes 214.

Figure 3:
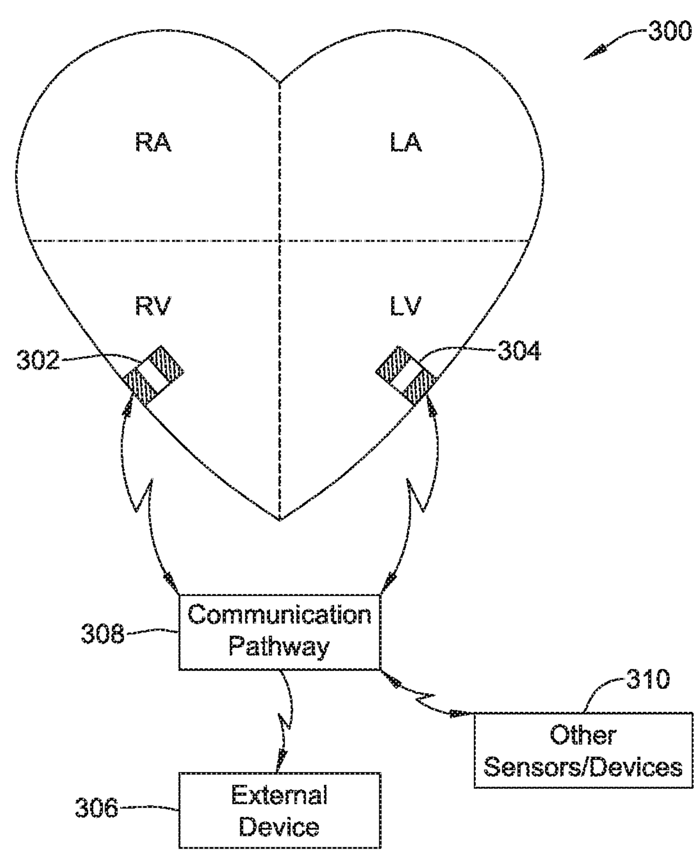
FIG. 3 is a schematic diagram of an exemplary medical system that includes multiple LCPs and/or other devices in communication with one another.

FIG. 3 illustrates an embodiment of a medical device system and a communication pathway through which multiple medical devices 302, 304, 306, and/or 310 of the medical device system may communicate. In the embodiment shown, medical device system 300 may include LCPs 302 and 304, external medical device 306, and other sensors/devices 310. External device 306 may be a device disposed external to a patient's body, as described previously with respect to MD 200. In at least some examples, external device 306 may represent an external support device such as a device programmer, as will be described in more detail below. Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one embodiment, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway 308. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some embodiments, the various devices of system 300 may communicate via pathway 308 using multiple signal types. For instance, other sensors/device 310 may communicate with external device 306 using a first signal type (e.g. RF communication) but communicate with LCPs 302/304 using a second signal type (e.g. conducted communication). Further, in some embodiments, communication between devices may be limited. For instance, as described above, in some embodiments, LCPs 302/304 may communicate with external device 306 only through other sensors/devices 310, where LCPs 302/304 send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. a voltage and/or current waveform punctuated with current and/or voltage pulses, referred herein as electrical communication pulses) into the patient's body via one or more electrodes of a transmitting device, and may receive the conducted communication signals via one or more electrodes of a receiving device. The patient's body may "conduct" the conducted communication signals from the one or more electrodes of the transmitting device to the electrodes of the receiving device in the system 300. In such embodiments, the delivered conducted communication signals may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses have an amplitude/pulse width designed to not capture the heart. In some cases, the amplitude/pulse width of the delivered electrical communication pulses may be above the capture threshold of the heart, but may be delivered during a refractory period of the heart and/or may be incorporated in or modulated onto a pacing pulse, if desired.

Additionally, unlike normal electrical stimulation therapy pulses, the electrical communication pulses may be delivered in specific sequences which convey information to receiving devices. For instance, delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, a predefined sequence of communication pulses may represent a corresponding symbol (e.g. a logic "1" symbol, a logic "0" symbol, an ATP therapy trigger symbol, etc.). In some cases, conducted communication pulses may be voltage pulses, current pulses, biphasic voltage pulses, biphasic current pulses, or any other suitable electrical pulse as desired.

Figure 4:
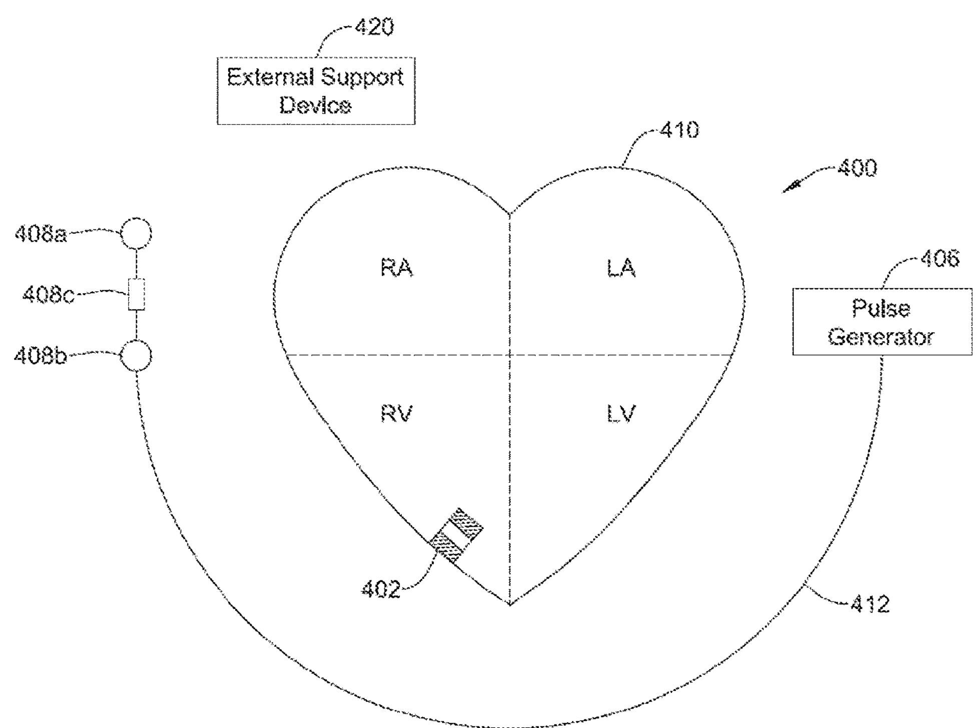
FIG. 4 is a schematic diagram of a system including an LCP and another medical device, in accordance with another embodiment of the present disclosure.

FIG. 4 depicts an illustrative medical device system 400 that may be configured to operate together. For example, system 400 may include multiple devices that are implanted within a patient and are configured to sense physiological signals, determine occurrences of cardiac arrhythmias, and deliver electrical stimulation to treat detected cardiac arrhythmias. In some embodiments, the devices of system 400 may be configured to determine occurrences of dislodgment of one or more devices of system 400. In FIG. 4, an LCP 402 is shown fixed to the interior of the right ventricle of the heart 410, and a pulse generator 406 is shown coupled to a lead 412 having one or more electrodes 408*a*-408*c*. In some cases, pulse generator 406 may be part of a subcutaneous implantable cardioverter-defibrillator (SICD), and the one or more electrodes 408*a*-408*c* may be positioned subcutaneously adjacent the heart. LCP 402 may communicate with the SICD, such as via communication pathway 308. The locations of LCP 402, pulse generator 406, lead 412, and electrodes 408*a-c* depicted in FIG. 4 are just exemplary. In other embodiments of system 400, LCP 402 may be positioned in the left ventricle, right atrium, or left atrium of the heart, as desired. In still other embodiments, LCP 402 may be implanted externally adjacent to heart 410 or even remote from heart 410.

Medical device system 400 may also include external support device 420. External support device 420 can be used to perform functions such as device identification, device programming and/or transfer of real-time and/or stored data between devices using one or more of the communication techniques described herein, or other functions involving communication with one or more devices of system 400. As one example, communication between external support device 420 and pulse generator 406 can be performed via a wireless mode, and communication between pulse generator 406 and LCP 402 can be performed via a conducted communication mode. In some embodiments, communication between LCP 402 and external support device 420 is accomplished by sending communication information through pulse generator 406. However, in other embodiments, communication between the LCP 402 and external support device 420 may be via a communication module.

FIG. 4 only illustrates one example embodiment of a medical device system that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406, with at least one LCP capable of delivering defibrillation therapy. Still another example may include one or more LCPs implanted along with a transvenous pacemaker and with or without an implanted SICD. In yet other embodiments, the configuration or placement of the medical devices, leads, and/or electrodes may be different from those depicted in FIG. 4. Accordingly, it should be recognized that numerous other medical device systems, different from system 400 depicted in FIG. 4, may be operated in accordance with techniques disclosed herein. As such, the embodiment shown in FIG. 4 should not be viewed as limiting in any way.

In some embodiments, LCP 100 may be configured to modify operation of LCP 100 based on a determined behavioral state of a patient. LCP 100 may, for example, determine a behavioral state of the patient based on a signal generated by a sensor of LCP 100. The below described techniques detail more specifically how LCP 100 may determine the behavioral state of the patient, and which operation(s) the LCP 100 adjusts based on the determine behavioral state. Additionally, although the below described techniques are described with respect to LCP 100, the techniques may be applied by any suitable medical devices. For instance, a device such as MD 200 may include one or more of the sensors to determine a behavioral state of a patient. When so provided, such devices may make use of the disclosed techniques.

In some instances, the behavioral state of the patient may relate to a posture of the patient. In some of these embodiments, LCP 100 may include an accelerometer and may be configured to determine the posture of the patient based on signals sensed from the accelerometer. The accelerometer may be a three-axis accelerometer, but this is not required. For example, the accelerometer may have one or two axes.

Figure 5:
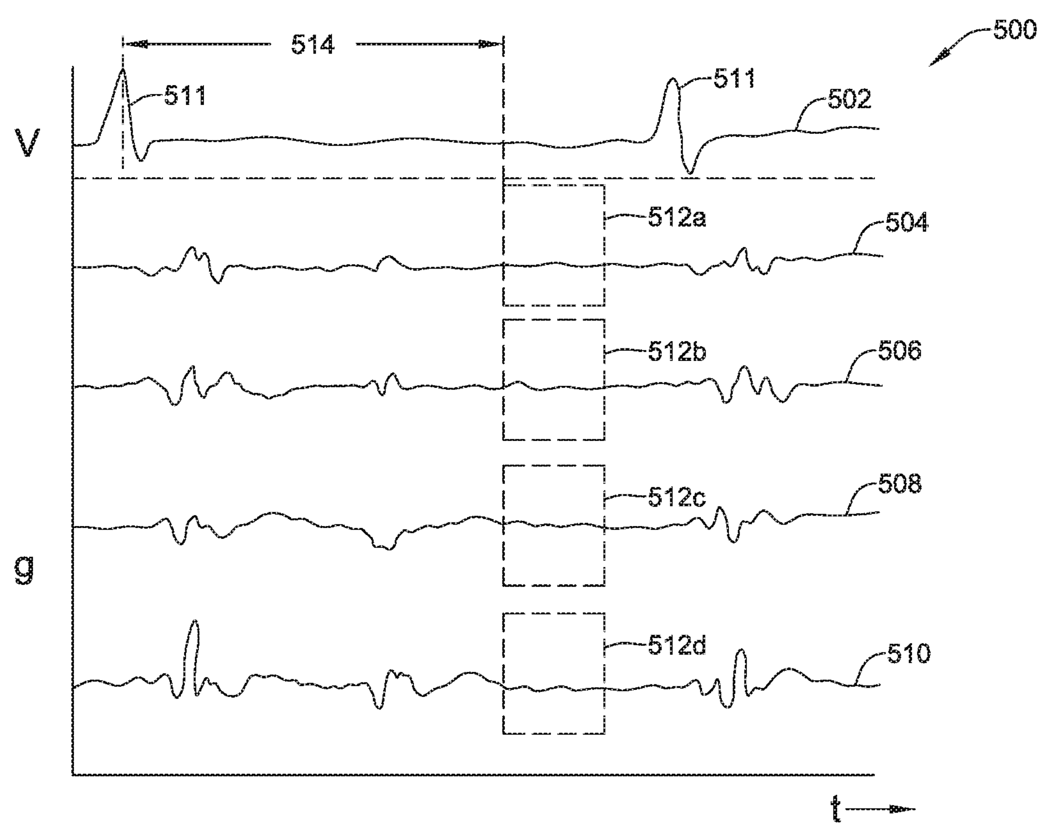
FIG. 5 is a graph showing an illustrative cardiac electrical signal along with corresponding accelerometer signals along a common time axis.

FIG. 5 is a graph 500 showing an illustrative cardiac electrical signal 502 (e.g. ECG) along with corresponding accelerometer signals 504, 506, 508 and 510 of a three axis accelerometer along a common time axis. The signal tracings of graph 500 may represent signals sensed or generated by an LCP 100 when LCP 100 is attached to a wall of a patients' heart. For example, signal 502 may represent a cardiac electrical signal 502 sensed by LCP 100. Signals 504, 506, and 508 may represent signals from different axes generated by a three-axis accelerometer of LCP 100. Signal 510 may represent an accelerometer magnitude signal, which may be determined by summing signals 504, 506, and 508 or summing the absolute values of signals 504, 506, and 508. In other embodiments, signal 510 may represent a different signal generated by other combinations of signals 504, 506, and 508, such as a root-mean-square or root-sum-square of signals 504, 506, and 508, or any other derivation of signals 504, 506, and 508.

LCP 100 may be configured to sense one or more of signals 504, 506, 508 and/or 510 during certain time periods. For instance, to "sense" one or more of the signals, it is contemplated that the LCP 100 may be configured to receive and process signals 504, 506, 508 and/or 510 at processing module 110. Whereas when the one or more of the signals are not being "sensed", processing module 110 of LCP 100 may not receive and/or process the signals 504, 506, 508 and/or 510. In some embodiments, to "sense" signals 504, 506, 508 and/or 510, LCP 100 may connect an output of the accelerometer to processing module 110 via a switch, multiplexer of the like. In other embodiments, the accelerometer may be configured to only output valid signals 504, 506, 508 and/or 510 when the accelerometer is to be sensed (e.g. the accelerometer may be enabled by processing module 110 when sensing is desired). In some cases, LCP 100 may control the generation of signals 504, 506, 508 and/or 510 by the accelerometer. For instance, LCP 100 may control when power is provided to the accelerometer, and the accelerometer may only generate signals 504, 506, 508 and/or 510 when power is provided to the accelerometer. In some cases, LCP 100 may switch the accelerometer from a lower-power state (e.g. a sleep mode) to a higher-power state (e.g. awake or active mode) during time periods where LCP 100 is to sense the accelerometer signal(s). During the lower-power state, the accelerometer may not provide an appreciable signal for LCP 100 to sense and/or sample. In some cases, and where processing module 110 is a digital device, an A/D converter may sample signals 504, 506, 508 and/or 510 when sensing is desired. These are just some examples of how signals 504, 506, 508 and/or 510 may be "sensed" during certain time periods.

LCP 100 may be configured to sense one or more signals during predetermined time periods. Such predetermined time periods may be represented by sensing periods 512*a*-512*d* in FIG. 5. Sensing periods 512*a*-512*d* may occur at regular intervals, such as every five seconds, every second, every eight hundred milliseconds, every seven hundred milliseconds, or any other suitable value. Alternatively, LCP 100 may initiate sensing periods 512*a*-512*d* after every beat, once every other beat, once every five beats, or at any other suitable frequency and/or duration. In at least some cases, LCP 100 may adjust the interval according to a heart rate of the patient such that successive sensing periods 512*a*-512*d* occur during the same portion of the cardiac cycle (e.g. when the heart is quiet such as between heart beats).

In some instances, LCP 100 may implement sensing periods 512*a*-512*d* based on one or more detected features of cardiac electrical signal 502. For instance, LCP 100 may detect one or more features of cardiac electrical signal 502, such as cardiac electrical events 511. Cardiac electrical events 511 may represent R-waves or other morphological features detected by LCP 100. Upon detection of cardiac electrical event 511, LCP 100 may initiate a time delay, such as time delay 514. Upon expiration of time delay 514, LCP 100 may initiate sensing periods 512*a*-512*d*, during which LCP 100 may "sense" one or more signals, such as signals 504, 506, 508 and/or 510. In at least some cases, LCP 100 may adjust time delay 514 based on the heart rate of the patient. For instance, when the heart rate is at a relatively higher heart rate, LCP 100 may shorten time delay 514, and when the heart rate is at a relatively lower heart rate, LCP 100 may lengthen time delay 514. This may help the LCP 100 consistently initiate sensing periods 512*a*-512*d* during the same or similar portion of the cardiac cycle (e.g. during the quit period between polarization/repolarizations of the heart).

In some instances, the length of time delay 514 may be chosen to align with a portion of the cardiac cycle where the heart is relatively mechanically inactive, such as shown in FIG. 5. For instance, time delay 514 may be chosen so that it expires between about fifty milliseconds to about one-hundred fifty milliseconds before the beginning of the next heartbeat. During this portion of the cardiac cycle, the heart muscle may be in a relatively relaxed state while filling with blood. Accordingly, during this portion of the cardiac cycle, the orientation of LCP 100 may be at a relatively consistent position. This may allow LCP 100 to more easily detect a current posture of the patient, as explained in more detail below. In other embodiments, an accelerometer or other sensor may be implanted in the patient outside of the heart, and may transmit an indication of posture to the LCP 100.

Figure 6:
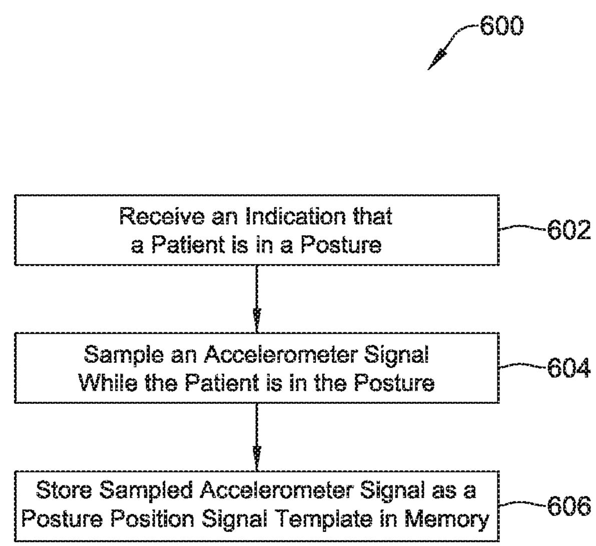
FIG. 6 is a flow diagram of an illustrative method of programming a medical device.
Figure 7:
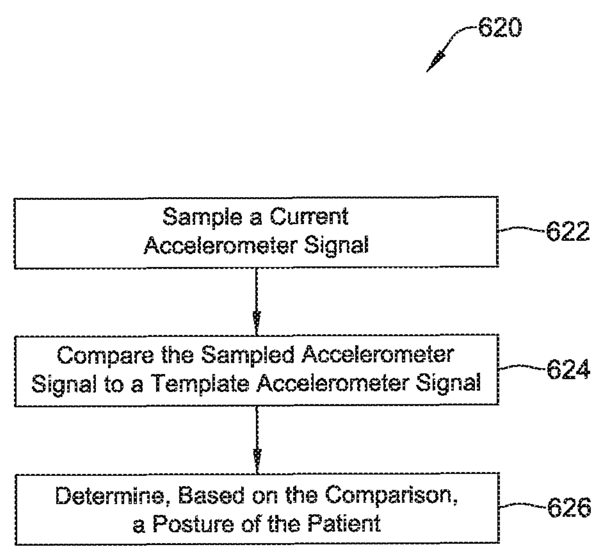
FIG. 7 is a flow diagram of an illustrative method of determining a posture.

FIGS. 6 and 7 depict flow diagrams of exemplary methods of how LCP 100 may determine a posture of the patient. FIG. 6 depicts a flow diagram of a method 600 of how an LCP 100 can be programmed according to different postures of the patient. In the example shown, once LCP 100 has been implanted within a patient's heart, LCP 100 may receive an indication that the patient is in a defined posture, as shown at 602. For instance, the patient may be positioned in an upright posture, and this may be communicated to the LCP 100 via an external support device, such as external support device 420, which in some embodiments may be a device programmer. A physician may physically verify that the patient is in an upright posture before causing the device programmer to communicate the posture to the LCP 100.

Once LCP 100 has received the indication of posture, LCP 100 may sample the accelerometer signal, as shown at 604. For instance, LCP 100 may provide power to the accelerometer so that the accelerometer may generate an accelerometer signal, and LCP 100 may sample the accelerometer signal for a predefined period of time while the patient is in the defined posture. In embodiments where the accelerometer is always generating an accelerometer signal, LCP 100 may simply be activated to sample the generated signal during the predefined period of time while the patient is in the defined posture.

In at least some embodiments, LCP 100 may only capture a single sample of the accelerometer signal during this programming. From this single captured sample, LCP 100 may generate a high accelerometer signal value and a low accelerometer signal value. For instance, LCP 100 may generate high and low accelerometer signal values that are about one percent, about two percent, about three percent, about five percent, about eight percent, about ten percent, or about fifteen percent, or another other suitable percentage values, higher and lower than the sampled value. LCP 100 may use these high and low accelerometer signal values as a template for the indicated posture.

Throughout this disclosure, the term 'accelerometer signal' may refer generally to one or all signals generated by the accelerometer, for example signals 504, 506, 508 and/or 510. Where LCP 100 is a three-axis accelerometer, the accelerometer may generate a signal for each of its three axes at the same time. These separate signals may be referred to as the 'accelerometer signal' herein for ease of description and the described steps or analyses may be performed on each of the signals. For instance, when LCP 100 senses or samples the accelerometer signal, LCP 100 may sense or sample each of the generated accelerometer signals. Accordingly, when LCP 100 senses the accelerometer signal during specific collection periods, such as sensing periods 512*a*-512*d*, LCP 100 may sense each of the signals representing the different axes of the accelerometer during the specific sensing periods. Similarly, where LCP 100 processes the accelerometer signal, LCP 100 may process each of the accelerometer signals in the same manner. In some cases, the LCP may only process a sub-set of the available accelerometer signals, such as just combination signal 510.

Once LCP 100 has sensed or sampled the accelerometer signal, LCP 100 may store the sensed or sampled accelerometer signal in memory, as shown at 606. This stored accelerometer signal may represent a template corresponding to the defined posture. In some cases, stored accelerometer signal is processed to develop an envelope and/or to extract certain features from the stored accelerometer signal to define a template that corresponds to the defined posture. This may be repeated for two or more different defined postures (e.g. an upright posture, a laying-down posture, a prone posture, a supine posture, a sitting posture, or any other suitable posture). As will be described in more detail below with regard to FIG. 7, LCP 100 may use the stored templates to determine a current posture of the patient.

Once LCP 100 has been programmed according to one or more defined postures, for instance by implementation of the illustrative method 600, LCP 100 may continually or periodically determine a current posture of the patient based on the sensed or sampled accelerometer signal of the LCP 100. FIG. 7 depicts a flow diagram of an illustrative method 620 of how LCP 100 may determine the current posture of the patient. LCP 100 may sense or sample a current accelerometer signal, as shown at 622. In some cases, LCP 100 may provide power to the accelerometer so that the accelerometer may generate an accelerometer signal, and LCP 100 may then sense or sample the accelerometer signal for a predefined time period.

LCP 100 may then compare the sensed or sampled accelerometer signal to one or more stored templates, as shown at 624. In some instances, LCP 100 may perform one or more correlation analyses, such as a cross-correlation analysis, between the sensed or sampled accelerometer signal and the one or more stored templates. For example, in a relatively simple approach, LCP 100 may determine an absolute value of the differences between a high value of the sampled accelerometer signal and a high value of the template and/or between a low value of the sampled accelerometer signal and a low value of the template. LCP 100 may then compare these values to one or more thresholds to determine if there is a match with a stored template. This is just one example. If a match is found, LCP 100 may determine that the current posture of the patient corresponds to the posture of the matching template, as shown at 626.

In embodiments where each template comprises a high and low accelerometer signal value, LCP 100 may compare the sensed accelerometer signal to the high and low accelerometer signal values of each template. LCP 100 may then determine the current posture to be the posture corresponding to the high and low accelerometer signal values between which the current sensed accelerometer signal falls.

Alternatively, LCP 100 may implement more complicated processes to determine a current posture. As one example, where LCP 100 includes a three-axis accelerometer, LCP 100 may determine vector differences between the current sensed accelerometer signal and each of the posture templates, which also comprise vectors. LCP 100 may then determine an absolute value of the difference between the current sensed accelerometer signal vector and a template vector (e.g. the sum of the absolute differences in the values of each of the three channels) and compare this difference to a threshold. If LCP 100 determines that this difference for a given posture template is less than a threshold difference, then LCP 100 determines the current posture is the given posture. In alternative examples, LCP 100 may use other values, such as the sum square distances of the vectors to determine posture.

In still other alternative embodiments, LCP 100 may use other comparisons or processes than simple differences between the vectors. Rather, LCP 100 may use other general ways of comparing the vectors, such as using ratios or rolling average trending, or the like.

Further, LCP 100 may use combinations of less than all of the available channels to determine posture. For instance, LCP 100 may only use two of the three channels to determine a current posture, rather than all available channels.

In general, LCP 100 may use method 620 to determine the current posture of the patient once every minute, once every 5 minutes, once every ten minutes, once every thirty minutes, once every hour, once every two hours, once every three hours, or another other suitable time period. Alternatively, or in addition, LCP 100 may determine the current posture of the patient every heartbeat, every other heartbeat, every five heartbeats, or at any other suitable frequency.

Alternatively, or in addition, LCP 100 may determine the current posture of the patient based on one or more thresholds corresponding to the heart rate of the patient, for example if the heart rate rises above or falls below a heart rate threshold. Alternatively, or in addition, LCP 100 may be configured to determine the current posture of the patient based on one or more messages received from another device external to LCP 100. For instances, another LCP, an SICD, sensor or any other external device may sense the current posture of the patient and/or a change on posture and send a message indicating the sensed posture and/or change in posture to the LCP 100. These are just a few examples of other methods by which LCP 100 may determine and/or update the posture of the patient. It is contemplated that LCP 100 may use more than one of these example techniques, and any combination of these or other techniques, to determine and/or verify the current posture of the patient, as desired.

In some instances, the behavior state of the patient may relate to an activity level of the patient. For example, LCP 100 may track a patient activity level using the signals sensed during sensing periods 512*a*-512*d*. To determine the patient activity level, LCP 100 may determine a difference between the current sensed accelerometer signal and a previously sensed accelerometer signal, for example the accelerometer signal sensed during the immediately preceding sensing period. LCP 100 may generate a patient activity parameter based on this determined difference. In some instances, LCP 100 may store the determined difference and may generate new determined differences on a rolling basis as LCP 100 senses new current accelerometer signals. In some cases, LCP 100 may determine a patient activity parameter from multiple of these determined differences. For instance, LCP 100 may sum the differences together to produce a patient activity parameter. LCP 100 may compare the patient activity parameter to one or more thresholds to determine an activity level of the patient. A region between two thresholds, or above or below a threshold may represent a predetermined patient activity level. In some cases, the patient activity level may be a number and the patient activity level may simply be the patient activity parameter. In general, low patient activity levels may indicate relatively little patient activity or movement, as the difference between the current sensed accelerometer signal and the previously sensed accelerometer signal may be small. Likewise, larger determined differences may indicate relatively greater patient activity or movement. In some cases, the behavioral state of the patient may be a combination of both the posture of the patient and the patient activity level.

Figure 8:
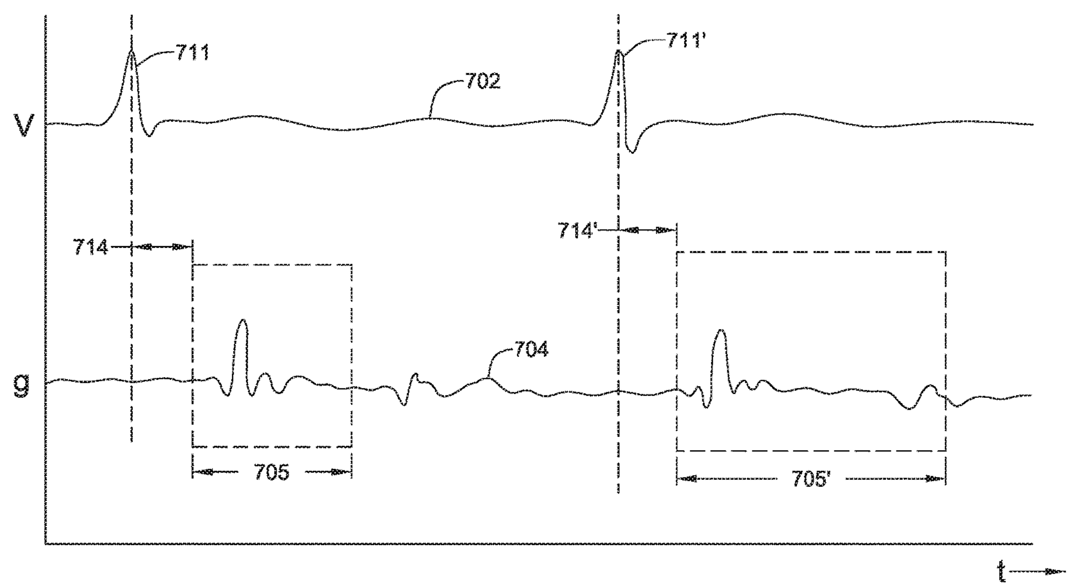
FIG. 8 is a graph of an illustrative cardiac electrical signal and corresponding accelerometer signal along a common time axis, including sensing periods during which a device may be programmed to sense the accelerometer signal.

In any of these embodiments, it is contemplated that the LCP 100 may be configured to change one or more ways in which LCP 100 operates based on the behavioral state of the patient. FIG. 8 depicts one example of how LCP 100 may change its operation. FIG. 8 depicts cardiac electrical signal 702 and accelerometer signal 704 on the same time axis. In the example of FIG. 8, LCP 100 may initially be operating according to an inactive behavior state. For instance, LCP 100 may have previously determined that the patient had a posture associated with an inactive behavior state (e.g. laying down), the patient activity level was below a threshold indicating an inactive behavior state, or both. While operating according to the inactive behavior state and upon detecting cardiac electrical event 711, LCP 100 may initiate sensing period 705 after a delay period 714. The delay period 714 may have a value such that sensing period 705 falls in a later portion of the cardiac cycle where the heart is relatively mechanically inactive, such as described above with respect to FIG. 5. Sensing period 705' may further have a delay period 714'. LCP 100 may collect accelerometer signal data during sensing period 705. For instance, processing module 110 of LCP 100 may sense or sample signal 704 generated by the accelerometer, or receive signal 704 or samples of signal 704 from the accelerometer. Based on the collected accelerometer data, LCP 100 may determine the posture of the patient and/or an activity level of the patient, as described previously.

In the example of FIG. 8, LCP 100 may determine, based on the accelerometer signal data collected during sensing period 705, that the behavioral state of the patient has changed. For instance, LCP 100 may determine that the posture of the patient has changed from a posture associated with an inactive behavioral state to a posture associated with an active behavioral state. Alternatively, LCP 100 may determine, based on the collected accelerometer signal data that the activity level of the patient has crossed a threshold indicating the patient is in an active behavioral state. In still further embodiments, LCP 100 may determine that both metrics indicate the patient is now in an active behavioral state.

After determining that the patient is in an active behavioral state, LCP 100 may adjust the length of the sensing period 705. For instance, during the next cardiac cycle, beginning with cardiac electrical event 711', LCP 100 may initiate sensing period 705'. Sensing period 705' may be initiated after a delay period 714', which in some embodiments may be the same delay period 714, and in other embodiments may be different than delay period 714. Additionally, sensing period 705' may have a length that is greater than the length of sensing period 705. In this manner, LCP 100 may observe the sensed accelerometer signal with greater resolution, e.g. for a greater length of time, at a higher sampling rate, and/or at higher bit count, during times where LCP 100 has determined that the patient is in an active behavioral state. Where LCP 100 also acts as a therapy delivery device, for example a pacemaker, this greater resolution may allow LCP 100 to more efficiently and/or effectively adjust the delivered therapy to match the physiological needs of the patient. In some cases, this may also allow the LCP 100 to save battery power by limiting the span of the sensing periods, reducing the sampling rate, and/or reducing the bit count, when the more accurate sensing it is not needed (e.g. during patient inactive time periods).

Although not shown in FIG. 8, LCP 100 may also determine when the patient transitions from an active behavioral state to an inactive behavioral state and/or visa-versa. For example, during sensing period 705', LCP 100 may determine that the posture of the patient has changed back to a posture associated with an inactive behavioral state, the actively level has fallen below a threshold, or both. In these examples, LCP 100 may switch back to using a sensing period having a shorter length than sensing period 705', reducing the sampling rate, and/or reducing the bit count.

FIG. 8 depicts just one example of how LCP 100 may be configured to change operation based on a determined change in behavioral state of the patient. In additional or alternative embodiments, LCP 100 may change the sampling rate. For instance, LCP 100 may increase the sampling rate of the accelerometer (or other sensor) signal after determining a change from an inactive behavioral state to an active behavioral state. Likewise, LCP 100 may decrease the sampling rate of the accelerometer (or other sensor) signal after determining a change from an active behavioral state to an inactive behavioral state.

In some further additional or alternative embodiments, LCP 100 may adjust the operation of the accelerometer upon determining changes in the patient's behavioral state. For instance, the accelerometer may be configured to operate in multiple modes. Some example modes may include a sleep mode, where the accelerometer does not produce an appreciable signal, and an awake mode where the accelerometer does produce a signal suitable for further processing. In some instances, the accelerometer may have multiple awake modes. For instance, the accelerometer may have a low-power awake mode where the accelerometer produces samples of the accelerometer signal at a rate of between about 1 Hz to about 2 Hz and wherein the accelerometer produces the signal or samples of the signal with a bit count of about 6 bits to about 8 bits. The accelerometer may have a high-power awake mode where the accelerometer produces samples of the accelerometer signal at a rate of between about 200 Hz to about 400 Hz and wherein the accelerometer produces the signal or samples of the signal with a bit count of about 12 bits to about 16 bits. In these instances, LCP 100, upon determination of a change from an inactive behavioral state to an active behavioral state, may change the accelerometer from the sleep-mode to any awake mode or from the low-power awake mode to the high-power awake mode. LCP 100 may do the opposite after determining a change from an active behavioral state to an inactive behavioral state. In some cases, the accelerometer may have additional awake modes where the accelerometer produces samples of the accelerometer signal with other combinations of sampling rate and/or bit count.

In some cases, LCP 100 may determine whether the patient is in one of multiple active behavioral states. When so provided, as LCP 100 determines changes from relatively less active behavioral states to relatively more active behavioral states, LCP 100 may transition the accelerometer from the sleep-mode to the low-power awake mode and then from the low-power awake mode to the high-power awake mode. As one example, LCP 100 may determine the patient has transitioned from an inactive behavioral state to a low-active behavioral state after determining a change in posture of the patient. LCP 100 may be configured to transition the accelerometer from the sleep-mode to the low-power awake mode, or from the low-power awake mode to another, higher-power awake mode. LCP 100 may then determine that the patient has transitioned from a low-active behavioral state to a high-active behavioral state after determining that the activity level of the patient increased above a threshold. LCP 100 may then transition the accelerometer from the low-power awake mode, or another, higher-power awake mode, to the high-power awake mode. Again, LCP 100 may perform the reverse of these operations as LCP 100 determines transitions in the patient's behavioral state from relatively more active behavioral states to relatively less active behavioral states.

In additional or alternative embodiments, LCP 100 may change the frequency of sensing periods based on a determined behavioral state of the patient. For instance, in an inactive behavioral state, LCP 100 may initiate sensing periods once every other cardiac cycle (e.g. after every other detected R-wave), once every third cardiac cycle, once every fifth cardiac cycle, once every eighth cardiac cycle, or any other suitable frequency. When LCP 100 determines a transition from a relatively less active behavioral state to relatively more active behavioral state, LCP 100 may increase the frequency of sensing periods. In at least some embodiments, where LCP 100 has multiple levels of active behavioral states, LCP 100 may associate a different frequency with each active behavioral state such that the frequency of sensing increases as LCP 100 determines transitions from less active behavioral states to more active behavioral states. Likewise, LCP 100 may decrease the frequency of sensing after a determination of a transition from relatively more active behavioral states to relatively less active behavioral states, if desired.

The above described embodiments focused on changes to an accelerometer or changes in how LCP 100 generates or senses an accelerometer signal based on determined behavioral state of the patient. However, in some cases, LCP 100 may additionally, or alternatively, adjust operation of other sensors of LCP 100. For instance, LCP 100 may include sensors for sensing different physiological parameters of the patient, such as gyroscopes, temperature sensors, pressure sensors, flow sensors, and blood-oxygenation sensors. LCP 100 may adjust the operation of any or all of the available sensors based on determined changes in behavioral states. The operation of such sensors may be adjusted in a manner similar to that described above with respect to the accelerometer. In some cases, LCP 100 may turn on or off one or more sensing modes. For instance, when transitioning from a relatively less active behavioral state to a relatively more active behavioral state, LCP 100 may initiate Atrial-Ventricle (AV) timing sensing and/or T-wave sensing. Where LCP 100 acts as a therapy delivery device, these additional sensed parameters may help LCP 100 more efficiently and/or effectively deliver therapy to the patient.

In some instances, LCP 100 may wait until LCP 100 has determined over the course of multiple successive sensing periods that the behavioral state has changed relative to a previous behavioral state. That is, instead of changing its operation based on a single determination of a transition in behavioral states, LCP 100 may wait to confirm that the patient is in the new behavioral state over multiple successive sensing periods. If the patient is confirmed to be in the new behavioral state, LCP 100 may change its operation according to the above techniques. In some cases, LCP 100 may confirm a behavior state change over three, four, five or more successive sensing periods. In some cases, LCP 100 may sense over a predetermined number of sensing periods, such as three, four, or five sensing periods, and may change operation only after determining the behavioral state is found in the new behavioral state in a majority, a super majority or all of the sensing periods.

As mentioned, in some instances, LCP 100 may operate as a therapy delivery device such as a pacemaker. When so provided, LCP 100 may deliver electrical stimulation pulses, such as pacing pulses, to the heart of the patient via electrodes 114/114' in order to cause the heart to contract. In some cases, LCP 100 may deliver the electrical stimulation pulses in a rate adaptive manner. For instance, LCP 100 may use one or more sensed signals and/or determined parameters based on the sensed signals to adjust a pacing rate, e.g. the rate of delivery of the electrical stimulation pulses to the heart. The signals and/or parameters may provide an indication of the cardiac load. The cardiac output of the heart may be matched to the cardiac load by, for example, increasing or decreasing the pacing rate.

In some cases, LCP 100 may adjust the pacing rate based on the positional and/or behavioral state of the patient. For instance, when LCP 100 detects when the patient transitions from relatively less active behavioral state to a relatively more active behavioral state, LCP 100 may increase the pacing rate. In some cases, LCP 100 may use other algorithms to calculate a pacing rate that is responsive to patient activity, such as determining a pacing rate based on the respiration of the patient and/or temperature of the blood in the patient. However, these other algorithms may react slower to changes in positional and/or behavioral states of a patient. Thus, and in some instances, adjust the pacing rate based on the positional and/or behavioral state of the patient may allow the pacing rate to be adjusted more quickly and may remain in control until the other slower reacting rate responsive pacing algorithms become effective. In some cases, this may help reduce orthostatic hypotension.

Figure 9:
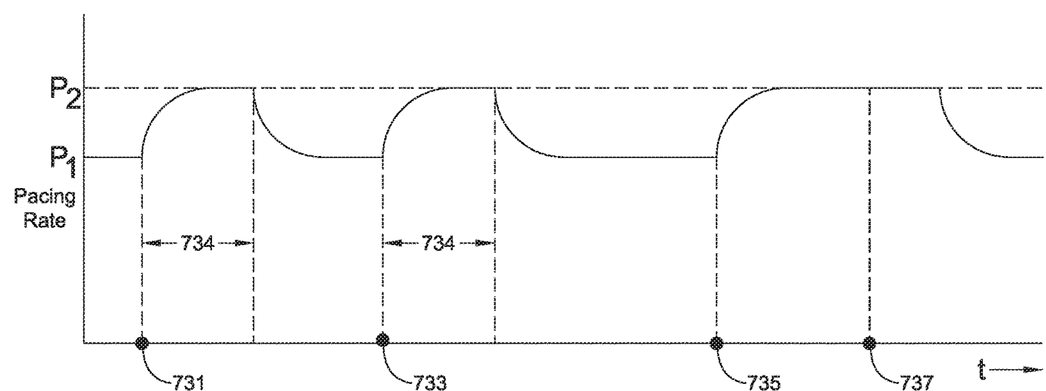
FIG. 9 is a graph showing an illustrative pacing rate versus time based on sensed behavior state changes.

One example of how LCP 100 may operate is shown in FIG. 9. FIG. 9 is a graph 730 showing an illustrative pacing rate versus time based on sensed behavior state changes. At time 731, LCP 100 may determine a change in a behavioral state of the patient, for example a change in the posture of the patient from a non-upright posture, e.g. laying-down or prone or supine, to an upright posture. Upon determining this change, LCP 100 may temporarily increase the pacing rate, as seen in FIG. 9. As depicted, LCP 100 may ramp up the pacing rate from $P_1$ to $P_2$. The change from $P_1$ to $P_2$ may represent LCP 100 changing the pacing rate by a predetermined amount, or may represent LCP 100 increasing the pacing rate to a predetermined level, $P_2$. Once at rate $P_2$, LCP 100 may maintain this pacing rate for a predetermined length of time 734. Upon expiration of length of time 734, LCP 100 may ramp down the pacing rate back to level $P_1$.

In some cases, LCP 100 may implement a similar functionality after determining a change from an upright posture to a non-upright posture. For instance, at time 733, LCP 100 may determine a change in posture of the patient from an upright posture to a non-upright posture. Upon making this determination, LCP 100 may increase the pacing rate from $P_1$ to $P_2$, and may maintain this rate for a length of time 734. Upon expiration of length of time 734, LCP 100 may ramp the pacing rate back down to level $P_1$.

As shown in FIG. 9, the change from level $P_1$ to $P_2$ is shown as a logarithmic or natural logarithmic change. However, in some cases, the change from level $P_1$ to $P_2$ may be an immediate change. In still other embodiments, the LCP 100 may change the rate from level $P_1$ to $P_2$ in discrete steps. In general, these are only some example methods by which LCP 100 may change the pacing rate from level $P_1$ to $P_2$. Likewise, the transition from level $P_2$ back to $P_1$ is depicted as having a decaying exponential shape. However, the transition from level $P_2$ back to $P_1$ may be any suitable transition as desired.

In some additional or alternative embodiments, length of time 734 may represent a timer. In at least some cases, additional determinations of transitions from a non-upright posture to an upright posture during the length of time 734 may act to reset length of time 734. As one example, LCP 100 may determine a change in posture of the patient from a non-upright posture to an upright posture at time 735. Upon this determination, LCP 100 may increase the pacing rate and begin a timer, as discussed. However, while the timer is running, LCP 100, at time 737, may determine another transition from a non-upright posture to an upright posture. For instance, after time 735 but before time 737, the patient may have changed posture from an upright posture to a non-upright posture, and then again from the non-upright posture to the upright posture, as at time 737. In these embodiments, LCP 100 may reset the timer at time 737, thereby keeping the pacing rate at level $P_2$ for a longer period of time, as shown in FIG. 9.

In some additional or alternative embodiments, how LCP 100 adjusts the pacing rate based on the determined behavioral state of the patient may change based on one or more other factors. As one example, LCP 100 may change how much to increase the pacing rate after determining a transition from a non-upright posture to an upright posture based on the current pacing rate. For instance, for relatively higher current pacing rates, LCP 100 may increase the pacing rate relatively less after determining a transition from a non-upright posture to an upright posture than when LCP 100 is currently pacing at a relatively lower pacing rate. Likewise, LCP 100 may also or instead increase the pacing rate relatively less after determining a transition from a non-upright posture to an upright posture where a pressure related signal (e.g. DP/DT) sensed by LCP 100 is relatively higher than when the pressure signal (DP/DT) is relatively lower.

It should be understood that the pacing rate depicted in FIG. 9 based on the behavioral state of the patient is only one rate drive that LCP 100 may implement. For instance, LCP 100 may determine a number of different pacing rates based off of different signals or groups of signals. LCP 100 may then deliver electrical stimulation pulses at the highest rate of all of the determined pacing rates. In this manner, LCP 100 may implement a blended pacing rate drive. As one example, after LCP 100 determines a transition from a non-upright posture to an upright posture, LCP 100 may increase the pacing rate determined based on the posture of the patient. Where this increase makes the pacing rate based on the posture the highest rate, LCP 100 will deliver electrical stimulation pulses according to this posture pacing rate. However, after a length of time 734, as shown in FIG. 9, LCP 100 may begin to decrease the pacing rate determined based on the posture of the patient. As this pacing rate begins to fall, it may fall below another of the pacing rates determined by LCP 100, such as a pacing rate based on a respiration rate and/or blood temperature of the patient. When the pacing rate determined based on the posture falls below the pacing rate determined based on the respiration rate and/or blood temperature, LCP 100 may being to deliver electrical stimulation pulses at the rate indicated by the respiration pacing rate and/or blood temperature.

Figure 10:
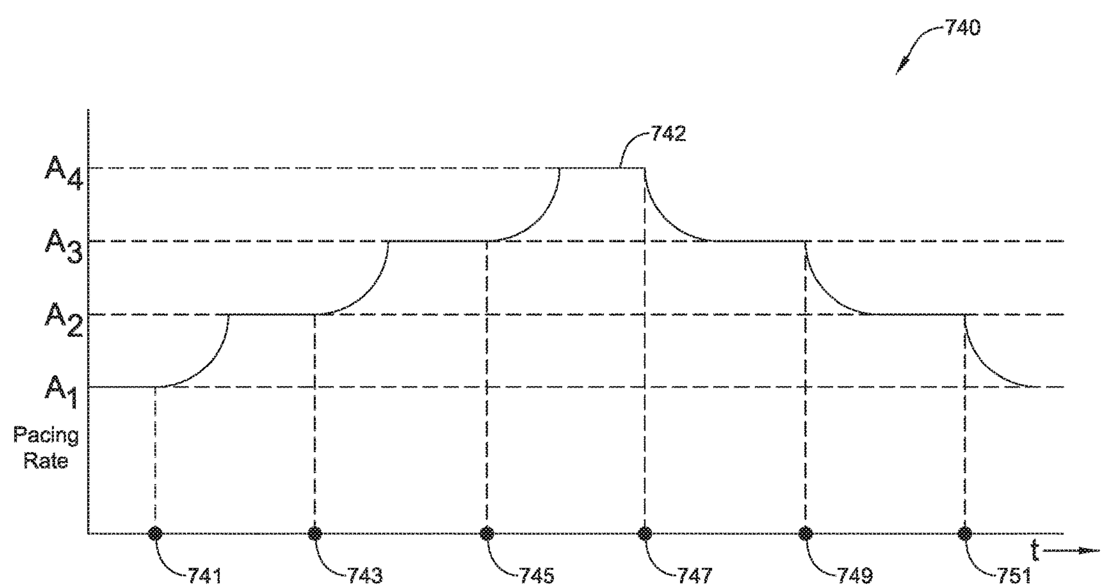
FIG. 10 is a graph showing another illustrative pacing rate versus time based on a sensed activity level of a patient.

In some cases, LCP 100 may use one or more signals or determined parameters to modify the current pacing rate, e.g. the highest of the rate drives, rather than determine a completely separate pacing rate based on the signal or signals or determined parameters. As one example, LCP 100 may track an activity level of the patient. FIG. 10 depicts an example of how LCP 100 may change the current pacing rate 742 based of the activity level of the patient. Current pacing rate 742 may represent the actual rate at which LCP 100 delivers electrical stimulation pulses to the patient's heart. In the example of FIG. 10, at time t=0, a patient activity parameter determined by LCP 100 may be at its lowest level, and LCP 100 may set the current pacing rate 742 at rate $A_1$. At time 741, LCP 100 may determine a change in the patient activity parameter from a first activity level to a next highest activity level, such as from a lowest level to a first, higher level. For instance at time 741, LCP 100 may determine that the patient activity parameter crossed a first threshold. Upon determining this change, LCP 100 may adjust the current pacing rate 742 from rate $A_1$ to rate $A_2$, as shown in FIG. 10. LCP 100 may maintain this new pacing rate while the patient activity parameter stays above the first threshold. At time 743, LCP 100 may determine that the patient activity parameter has increased above a second, even higher threshold. Accordingly, and in the example shown, LCP 100 may increase the current pacing rate 742 to rate $A_3$ and maintain this increased pacing rate. At time 745, LCP 100 may determine that the patient activity parameter has increased above a third, still higher threshold, and may increase the current pacing rate 742 to $A_4$, and maintain this new pacing rate while the patient activity parameter stays above the third threshold.

In a similar manner, LCP 100 may decrease the current pacing rate 742 as LCP 100 determines that the patient activity parameter has fallen below the first, second, and/or third thresholds (or other thresholds). In the example shown in FIG. 10, LCP 100 may determine at time 747 that the patient activity parameter has fallen below the third threshold, and may decrease the current pacing rate 742 back to rate $A_3$. Similarly, at times 749 and 751, LCP 100 may determine that patient activity parameter has fallen below the second and first thresholds, respectively, and may decrease the current pacing rate 742 to rate $A_2$ and then to rate $A_1$. In some cases, the thresholds used when decreasing the pacing rate may be different from those used when increasing the pacing rate. In some cases, this may be useful to provide a level of hysteresis, which can be help reduce changes in the pacing rate when the patient activity parameter moves about one of the thresholds.

Although the example of FIG. 10 shows sequential changes in the patient activity parameter, LCP 100 may operate in a similar manner where LCP 100 determines that the patient activity parameter, when below one threshold, rises above the next two or more thresholds. For instance, in the example of FIG. 10, if LCP 100 determined that, while current pacing rate 742 is at rate $A_1$, that the patient activity parameter rose above the third threshold, LCP 100 may increase current pacing rate 742 from rate $A_1$ to rate $A_4$.

Additionally, although graphs 740 shows current pacing rate 742 increasing and decreasing in a somewhat exponential manner, it should be understood that in other examples the shape of the ramp ups and ramp downs may differ. For instance, the shape of the ramp ups and ramp downs may be logarithmic or natural logarithmic, have constant slopes, may include discrete steps, or may assume any other suitable shape.

In some instances, the new, higher pacing rate 742 may be added to another calculated pacing rate, e.g. a pacing rate determined based on a respiration signal, a blood temperature signal, etc. The other calculated pacing rate may react slower to changes in positional and/or behavioral states of a patient. When so provided, the current pacing rate 742 may fluctuate up or down as the other calculated pacing rate changes over time, but may remain above the other calculated pacing rate by the pacing rate 742. In other instances, the new pacing rate set by LCP 100 may not be added to the other calculated pacing rate, but rather may act as a floor for the pacing rate. When so provided, if the other calculated pacing rate rises above the pacing rate 742, the other calculated pacing rate may take over and drive the pacing rate of the heart.

In some alterative embodiments, instead of adjusting current pacing rate 742 directly, LCP 100 may instead adjust a lower rate limit (LRL), which may indirectly adjust the current pacing rate 742. The LRL may act as a low threshold or floor for the pacing rate. For instance, if all determined pacing rates fall below the LRL, LCP 100 may still pace the patient's heart at least as fast as the LRL. Accordingly, and in some instances, after determining an increase in the patient activity parameter, LCP 100 may increase the LRL. Likewise, if LCP 100 determines that the patient activity parameter has fallen from the current level, LCP 100 may lower the LRL. If any of the determined pacing rates are above the new LRL, LCP 100 will pace at the higher rate.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. A method for operating a leadless cardiac pacemaker implanted into a patient, the patient having two or more predefined behavioral states including a first predefined behavioral state and a second predefined behavioral state, the method comprising:

the leadless cardiac pacemaker detecting a change in the behavioral state of the patient from the first predefined behavioral state to the second predefined behavioral state, and in response, the leadless cardiac pacemaker changing a sampling rate of a sensor signal generated by a sensor of the leadless cardiac pacemaker from a first sampling rate to a second sampling rate;

the leadless cardiac pacemaker using the sampled sensor signal at the second sampling rate to determine an updated pacing rate of the leadless cardiac pacemaker; and the leadless cardiac pacemaker providing pacing to the patient at the updated pacing rate.

2. The method of claim 1, wherein the sensor has a lower power mode and a higher power mode, and wherein the leadless cardiac pacemaker uses the sensor in the lower power mode to detect the change in the behavioral state of the patient from the first predefined behavioral state to the second predefined behavioral state, and in response to detecting the change in the behavioral state of the patient, the leadless cardiac pacemaker switching the sensor to the higher power mode.

3. The method of claim 2, wherein the lower power mode is a low power sleep mode, and the higher power mode is an awake mode.

4. The method of claim 1, wherein the change in the behavioral state of the patient from the first predefined behavioral state to the second predefined behavioral state corresponds to a change in a posture of the patient.

5. The method of claim 1, wherein the change in the behavioral state of the patient from the first predefined behavioral state to the second predefined behavioral state corresponds to a change in an activity level of the patient.

6. The method of claim 1, wherein the sensor is an accelerometer.

7. The method of claim 1, wherein the sensor is one or more of an impedance sensor, a pressure sensor, a flow sensor, a temperature sensor, a gyroscope, an acoustic sensor and a blood oxygenation sensor.

8. The method of claim 1, wherein, in response to detecting the change in the behavioral state of the patient from the first predefined behavioral state to the second predefined behavioral state, the leadless cardiac pacemaker further changing a sampling time window for sampling the sensor signal generated by the sensor of the leadless cardiac pacemaker.

9. The method of claim 1, wherein upon detecting a change from an inactive behavioral state as the first predefined behavioral state to an active behavioral state as the second predefined behavioral state, the leadless cardiac pacemaker determines an updated pacing rate that is increased to reduce orthostatic tension in the patient.

10. The method of claim 9, wherein upon detecting a change from the active behavioral state to the inactive behavioral state, the leadless cardiac pacemaker determines an updated pacing rate that is decreased.

11. The method of claim 9, wherein upon detecting a change from the active behavioral state to the inactive behavioral state, the leadless cardiac pacemaker decreasing the sampling rate of the sensor signal generated by the sensor of the leadless cardiac pacemaker.

12. The method of claim 10, wherein upon detecting a change from the inactive behavioral state to the active behavioral state, the leadless cardiac pacemaker increasing the sampling rate of the sensor signal generated by the sensor of the leadless cardiac pacemaker.

13. The method of claim 10, wherein upon detecting a change from the active behavioral state to the inactive behavioral state, the leadless cardiac pacemaker lowers the lower-rate-limit (LRL), and upon detecting a change from the inactive behavioral state to the active behavioral state, the leadless cardiac pacemaker raises the lower-rate-limit (LRL).

14. The method of claim 1, further comprises receiving an input from a user that defines one or more of the behavioral states, wherein the input is received via communication messages from an external programmer.

15. A method for operating a leadless cardiac pacemaker implanted into a patient, the patient having two or more predefined postures, the method comprising:

the leadless cardiac pacemaker sensing a predetermined physiological parameter using a sensor, the leadless cardiac pacemaker capable of sensing the predetermined physiological parameter in a lower power sensing mode with less resolution and a higher power sensing mode with more resolution;

the leadless cardiac pacemaker detecting a change from a first one of the two or more predefined postures to a second one of the two or more predefined postures, and in response, the leadless cardiac pacemaker changing from the lower power sensing mode to the higher power sensing mode;

the leadless cardiac pacemaker using the sensed physiological parameter to determine an updated pacing rate of the leadless cardiac pacemaker; and the leadless cardiac pacemaker providing pacing to the patient at the updated pacing rate.

16. The method of claim 15, wherein:

the leadless cardiac pacemaker detecting a change from the second one of the two or more predefined postures to the first one of the two or more predefined postures, and in response, the leadless cardiac pacemaker changing from the higher power sensing mode to the lower power sensing mode.

17. A leadless cardiac pacemaker (LCP), comprising:

a plurality of electrodes;

an accelerometer;

a controller connected to the plurality of electrodes and the accelerometer, the controller configured to:

sense an acceleration signal generated by the accelerometer, the controller capable of sensing the acceleration signal in a lower power sensing mode with less resolution and a higher power sensing mode with more resolution;

detect a change from a first one of two or more predefined postures via the acceleration signal to a second one of the two or more predefined postures, and in response, change from the lower power sensing mode to the higher power sensing mode;

using the sensed acceleration signal to determine an updated pacing rate; and providing pacing to the patient at the updated pacing rate.

18. The leadless cardiac pacemaker (LCP) of claim 17, wherein in the higher power sensing mode, the acceleration signal is sampled at a higher sampling rate than in the lower power sensing mode.

19. The leadless cardiac pacemaker (LCP) of claim 17, wherein in the higher power sensing mode, the acceleration signal is sampled in a longer sampling time window than in the lower power sensing mode.

20. The leadless cardiac pacemaker (LCP) of claim 17, wherein the pacing is provided via two or more of the plurality of electrodes.

* * * * *